(12) United States Patent
Warner et al.

(10) Patent No.: US 9,630,981 B2
(45) Date of Patent: Apr. 25, 2017

(54) PROCESSES FOR PREPARING FUNCTIONALIZED F-POSS MONOMERS

(71) Applicant: NBD Nanotechnologies, Inc., Danvers, MA (US)

(72) Inventors: John C. Warner, Wilmington, MA (US); Jean R. Loebelenz, Essex, MA (US); Srinivasa Rao Cheruku, Lexington, MA (US); Thomas Woodrow Gero, Stow, MA (US)

(73) Assignee: NBD Nanotechnologies, Inc., Danvers, MA (US)

( * ) Notice: Subject to any disclaimer, the term of this patent is extended or adjusted under 35 U.S.C. 154(b) by 0 days.

(21) Appl. No.: 15/048,464

(22) Filed: Feb. 19, 2016

(65) Prior Publication Data
US 2016/0326191 A1     Nov. 10, 2016

Related U.S. Application Data

(60) Provisional application No. 62/118,220, filed on Feb. 19, 2015.

(51) Int. Cl.
     *C07F 7/21*         (2006.01)
     *C07F 7/08*         (2006.01)

(52) U.S. Cl.
     CPC ............ *C07F 7/0876* (2013.01); *C07F 7/21* (2013.01)

(58) Field of Classification Search
     USPC ........................................................ 556/446
     See application file for complete search history.

(56) References Cited

U.S. PATENT DOCUMENTS

| 6,660,823 | B1 | 12/2003 | Lichtenhan et al. |
| 2008/0221262 | A1 | 9/2008 | Mabry et al. |

FOREIGN PATENT DOCUMENTS

WO     0110871 A1     2/2001

OTHER PUBLICATIONS

Ramirez et al Polym. Preprints., 2011, 52(1), ; Abstract (American Chemical Society, Division of Polymer Chemistry).*
Chhatre et al.; Fluoroalkylated Silicon-Containing Surfaces—Estimation of Solid Surface Energy; ACS Appl. Mater. Interfaces; 2010; pp. 3544-3554; vol. 2.
Mabry et al.; Fluorinated Polyhedral Oligomeric Silsesquioxanes (F-POSS); Angew. Chem.; Int. Ed. 2008; pp. 4137-4140; vol. 47.
Rameriz et al.; Incompletely Condensed Fluoroalkyl Silsesquioxanes and Derivatives: Precursors for Low Surface Energy Materials; J. Am. Chem. Soc.; 2011; pp. 20084-20087; vol. 133.
Tuteja et al.; Superomniphobic Surfaces for Effective Chemical Shielding; Science; 2007; pp. 1618-1622; vol. 318.
Tuteja et al.; Designing Superoleophobic Surfaces; Proc. Natl. Acad. Sci. U.S.A.; 2008; pp. S18200/1-S18200/29; vol. 105.
Search Report and Written Opinion for International Patent Application No. PCT/US2016/018584; Jul. 8, 2016.

* cited by examiner

*Primary Examiner* — Sudhakar Katakam
*Assistant Examiner* — Kofi Adzamli
(74) *Attorney, Agent, or Firm* — Jason A. Bernstein; Barnes & Thornburg LLP

(57) ABSTRACT

The present disclosure relates to compositions of matter comprising synthetic blends of at least two feedstocks that produce a distribution of fluorinated polyhedral oligomeric silsesquioxane compounds. The present disclosure also relates to methods of making such fluorinated polyhedral oligomeric silsesquioxane compounds from such synthetic blends. The present disclosure also relates to uses of such fluorinated polyhedral oligomeric silsesquioxane compounds.

20 Claims, 13 Drawing Sheets

PROCESSES FOR PREPARING FUNCTIONALIZED F-POSS MONOMERS

CROSS-REFERENCE TO RELATED APPLICATION

This patent application claims priority to U.S. Provisional Patent Application No. 62/118,220, filed Feb. 19, 2015, the disclosure of which is incorporated herein by reference in its entirety.

FIELD

The present disclosure relates, in exemplary embodiments, to compositions of matter comprising synthetic blends of at least two feedstocks that produce a distribution of fluorinated polyhedral oligomeric silsesquioxane molecule structures. The present disclosure also relates, in exemplary embodiments, to methods of making such synthetic blends.

BACKGROUND

Fluorinated polyhedral oligomeric silsesquioxane ("F-POSS") molecules are a subclass of polyhedral oligomeric silsesquioxanes ("POSS") which consists of a silicon-oxide core [$SiO_{1.5}$] with a periphery of long-chain fluorinated alkyl groups. F-POSS molecules possesses one of the lowest known surface energies leading to the creation of superhydrophobic and oleophobic surfaces. A feature of F-POSS material is that it ordinarily forms a siloxy cage that acts like an inorganic glass-like material, but have organic R group substituents at the matrix apices, which provides unusual properties and applications. See Formula I below.

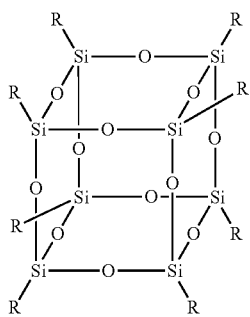

I

F-POSS molecules find application in material science. For example, superhydrophobic and superoleophobic surfaces have been produced using F-POSS, either cast on a substrate or blended into a polymer matrix. See for example Chhatre, S. S.; Guardado, J. O.; Moore, B. M.; Haddad, T. S.; Mabry, J. M.; McKinley, G. H.; Cohen, R. E. *ACS Appl. Mater. Interfaces* 2010, 2, 3544-3554; Mabry, J. M.; Vij, A.; Iacono, S. T.; Viers, B. D. *Angew. Chem., Int. Ed.* 2008, 47, 4137-4140; Tuteja, A.; Choi, W.; Mabry, J. M.; McKinely, G. H.; Cohen, R. E. *Proc. Natl. Acad. Sci.* U.S. Pat. No. 2,008,105, S18200/1S18200/29; and Tuteja, A.; Choi, W.; Ma, M.; Mabry, J. M.; Mazzella, S. A.; Rutledge, G. C.; McKinley, G. H.; Cohen, R. E. *Science* 2007, 318, 1618-1622.

Preparation of functionalized F-POSS molecules has been achieved with limited success. Early approaches involved the preparation of incompletely condensed silsesquioxanes. The most effective early approaches have involved the opening of completely condensed POSS cage edges by acid catalysis and isolation of disilanol fluorinated polyhedral oligomeric silsesquioxane (F-POSS-$(OH)_2$). The isolated F-POSS-$(OH)_2$ molecule has been subsequently treated with dichlorosilanes of the type $Cl_2SiR_1R_2$ to produce functionalized F-POSS structures. See, Ramirez, S. M.; Diaz, Y. J.; Campos, R.; Stone, R. L.; Haddad, T. S.; Mabry, J. M. *J. Am. Chem. Soc.*, 2011, 133, 20084-20087. A major drawback of such approaches is the difficulty in isolating the desired disilanol. Without being bound by theory, it is postulated that the completely condensed F-POSS cage exists in equilibrium with the ring-opened disilanol product under acidic conditions. Accordingly, the ring-opened disilanol is constantly undergoing condensation to the lower energy state of the completely condensed F-POSS cage. The instability of the disilanol intermediate results in low overall yields of functionalized F-POSS molecules, typically in the range of 25%-35% from the starting completely condensed F-POSS starting material.

It would be desirable to provide an efficient, high-yield process for producing functionalized F-POSS molecules for use in materials.

SUMMARY

In some embodiments, the description provides a process for preparing a derivatized F-POSS of the formula

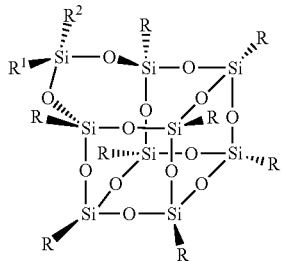

II comprising the step of contacting at least one F-POSS molecule of the formula

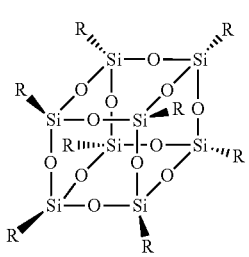

I with a compound of the formula $R^1R^2Si(OR^3)_2$,
wherein R is a long chain fluorinated alkyl; $R^1$ and $R^2$ are each independently selected from the group consisting of $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^1$ and $R^2$ is independently optionally substituted by an $R^4$; $R^3$ is a $C_1$-$C_8$ alkoxy; each $R^4$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^5$, —NR$^5$R$^6$, —OC(O)R$^5$, —C(O)OR$^5$, —C(O)R$^5$, —OC(O)OR$^5$, —C(O)NR$^5$R$^6$, —OC(O)NR$^5$R$^6$, —NR$^5$C(O)R$^6$, —NR$^5$C(O)OR$^6$ and —NR$^5$C(O)NR$^5$R$^6$, and when R$^4$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in R$^4$ is independently optionally substituted by an R$^7$; each R$^5$ and R$^6$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, and 5-7 membered heteroaryl, wherein each hydrogen atom in R$^5$ and R$^6$ is independently optionally substituted by an R$^7$; each R$^7$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^8$, —NR$^8$R$^9$, —OC(O)R$^8$, —C(O)OR$^8$, —C(O)R$^8$, —OC(O)OR$^8$, —C(O)NR$^8$R$^9$, —OC(O)NR$^8$R$^9$, —NR$^8$C(O)R$^9$, —NR$^8$C(O)OR$^9$ and NR$^8$C(O)NR$^8$R$^9$, and when R$^7$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in R$^7$ is independently optionally substituted by an R$^{10}$; each R$^8$ and R$^9$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in R$^8$ and R$^9$ is independently optionally substituted by one or more R$^{10}$; each R$^{10}$ is independently selected from the group consisting of hydrogen, halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —OR$^{11}$, —NR$^{11}$R$^{12}$, —OC(O)R$^{11}$, —C(O)OR$^{11}$, —C(O)R$^{11}$, —OC(O)OR$^{11}$, —C(O)NR$^{11}$R$^{12}$, —OC(O)NR$^{11}$R$^{12}$, —NR$^{11}$C(O)R$^{12}$, —NR$^{11}$C(O)OR$^{12}$ and —NR$^{11}$C(O)NR$^{11}$R$^{12}$, and when R$^{10}$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, $C_3$-$C_8$ cycloalkyl or 5-7 membered heteroaryl, each hydrogen in R$^{10}$ is independently optionally substituted by a moiety selected from the group consisting of halo, —NCO, —OR$^{11}$, —NR$^{11}$R$^{12}$, —OC(O)R$^{11}$, —C(O)OR$^{11}$, —C(O)R$^{11}$, —OC(O)OR$^{11}$, —C(O)NR$^{11}$R$^{12}$, —OC(O)NR$^{11}$R$^{12}$, —NR$^{11}$C(O)R$^{12}$, —NR$^{11}$C(O)OR$^{12}$ and —NR$^{11}$C(O)NR$^{12}$; and each R$^{11}$ and R$^{12}$ is independently selected from the group consisting of H, $C_1$-$C_8$ alkyl, $C_2$-$C_8$ alkenyl and $C_2$-$C_8$ alkynyl, and when R$^{11}$ or R$^{12}$ are $C_1$-$C_8$ alkyl, $C_2$-$C_8$ alkenyl or $C_2$-$C_8$ alkynyl, each hydrogen atom in R$^{11}$ and R$^{12}$ is independently optionally substituted by a fluorine atom, in the presence of an aqueous base catalyst.

In one aspect of these embodiments, R$^1$ is $C_1$-$C_8$ alkyl, wherein each hydrogen atom in R$^1$ is independently optionally substituted by an R$^4$. In another aspect of these embodiments, R$^4$ is —NCO, —OR$^5$, —OC(O)R$^5$, —C(O)OR$^5$, —C(O)R$^5$ or —OC(O)OR$^5$. In another aspect of these embodiments, R$^5$ is $C_1$-$C_8$ alkyl, wherein each hydrogen atom in R$^5$ is independently optionally substituted by an R$^7$. In another aspect of these embodiments, R$^5$ is $C_2$-$C_8$ alkenyl, wherein each hydrogen atom in R$^5$ is independently optionally substituted by an R$^7$. In another aspect of these embodiments, R$^7$ is $C_1$-$C_8$ alkyl, —NCO, —OR$^8$, —NR$^8$R$^9$, —OC(O)R$^8$, —C(O)OR$^8$, —C(O)R$^8$ or —OC(O)OR$^8$. In another aspect of these embodiments, R$^8$ is $C_1$-$C_8$ alkyl, $C_2$-$C_8$ alkenyl, $C_2$-$C_8$ alkynyl, $C_6$-$C_{10}$ aryl or 5-7 membered heteroaryl, wherein each hydrogen atom in R$^8$ is independently optionally substituted by one or more R$^{10}$. In another aspect of these embodiments, R$^2$ is $C_1$-$C_8$ alkyl. In another aspect, R$^2$ is methyl.

In another aspect of these embodiments, R$^{10}$ is hydrogen or $C_1$-$C_8$ alkyl, and when R$^{10}$ is $C_1$-$C_8$ alkyl, R$^{10}$ is optionally substituted by a —OC(O)R$^{11}$. In another aspect of these embodiments, R$^{11}$ is H or $C_1$-$C_8$ alkyl, and when R$^{11}$ is $C_1$-$C_8$ alkyl, each hydrogen atom in R$^{11}$ is independently optionally substituted by a fluorine atom. In another aspect of these embodiments, R$^1$ is n-propyl, optionally substituted by an R$^4$. In another aspect of these embodiments, R$^4$ is —OC(O)R$^5$ or —OC(O)OR$^5$. In another aspect of these embodiments, R$^5$ is n-propyl, optionally substituted by an R$^7$. In another aspect of these embodiments, R$^5$ is —CH═CH$_2$, optionally substituted by an R$^7$. In another aspect of these embodiments, R$^7$ is $C_1$-$C_8$ alkyl. In another aspect of these embodiments, R$^7$ is methyl. In another aspect of these embodiments, R$^7$ is —OC(O)R$^8$ or —C(O)OR$^8$. In another aspect of these embodiments, R$^8$ is —CH═CH$_2$, optionally substituted by an R$^{10}$. In another aspect of these embodiments, R$^{10}$ is $C_1$-$C_8$ alkyl. In another aspect of these embodiments, R$^{10}$ is methyl. In another aspect of these embodiments, R$^1$ is $C_6$-$C_{10}$ aryl, wherein each hydrogen atom in R$^1$ is independently optionally substituted by an R$^4$. In another aspect of these embodiments, R$^4$ is $C_1$-$C_8$ alkyl, $C_2$-$C_8$ alkenyl or —NCO, and when R$^4$ is $C_1$-$C_8$ alkyl or $C_2$-$C_8$ alkenyl, each hydrogen atom in R$^4$ is independently optionally substituted by an R$^7$. In another aspect of these embodiments, R$^4$ is $C_2$-$C_8$ alkenyl, optionally substituted by an R$^7$. In another aspect of these embodiments, R$^4$ is —CH═CH$_2$, optionally substituted by an R$^7$. In another aspect of this embodiment, R$^7$ is methyl.

In another aspect of these embodiments, R$^4$ is $C_1$-$C_8$ alkyl, optionally substituted by an R$^7$. In another aspect of these embodiments, R$^7$ is $C_6$-$C_{10}$ aryl, optionally substituted by an R$^{10}$. In another aspect of these embodiments, wherein R$^{10}$ is $C_2$-$C_8$ alkenyl or —NCO, and when R$^{10}$ is $C_2$-$C_8$ alkenyl, R$^{10}$ is optionally substituted by a moiety selected from the group consisting of halo, —NCO, —OR$^{11}$, —NR$^{11}$R$^{12}$, —OC(O)R$^{11}$, —C(O)OR$^{11}$, —C(O)R$^{11}$, —OC(O)OR$^{11}$, —C(O)NR$^{11}$R$^{12}$, —OC(O)NR$^{11}$R$^{12}$, —NR$^{11}$C(O)R$^{12}$, —NR$^{11}$C(O)OR$^{12}$ and —NR$^{11}$C(O)NR$^{11}$R$^{12}$. In another aspect of these embodiments, R$^{10}$ is —CH═CH$_2$. In another aspect of these embodiments, R$^{10}$ is —NCO. In another aspect of these embodiments, R$^1$ is $C_2$-$C_8$ alkenyl, wherein each hydrogen atom in R$^1$ is independently optionally substituted by an R$^4$. In another aspect of these embodiments, R$^4$ is halo.

In another aspect of these embodiments, the aqueous base catalyst is an aqueous ammonium salt. In another aspect of these embodiments, the aqueous base catalyst is a tetraethylammonium salt. In another aspect of these embodiments, the aqueous base catalyst is tetraethylammonium hydroxide.

In another aspect of these embodiments, the long chain fluorinated alkyl is 8/2, 6/2, 4/2, or combinations thereof. In another aspect of these embodiments, the long chain fluorinated alkyl selected from the group consisting of 8/2, 6/2 and 4/2. In another aspect of these embodiments, the at least one F-POSS molecule is selected from the group consisting of 8/2 F-POSS, 6/2 F-POSS and 4/2 F-POSS. In another aspect of these embodiments, the at least one F-POSS molecule is 6/2 F-POSS. In another aspect of these embodiments, the at least one F-POSS molecule is 4/2 F-POSS. In another aspect of these embodiments, the long chain fluorinated alkyl is 6/2.

In another aspect of these embodiments, the long chain fluorinated alkyl is 4/2. In another aspect of these embodiments, the F-POSS molecule is a synthetic blend F-POSS molecule wherein R is a combination of independently selected long chain fluorinated alkyls. In one aspect of this embodiment, R is a combination of two long chain fluorinated alkyls independently selected from the group consisting of 8/2, 6/2 and 4/2.

DEFINITIONS

Figures 1A, 1B, 1C:
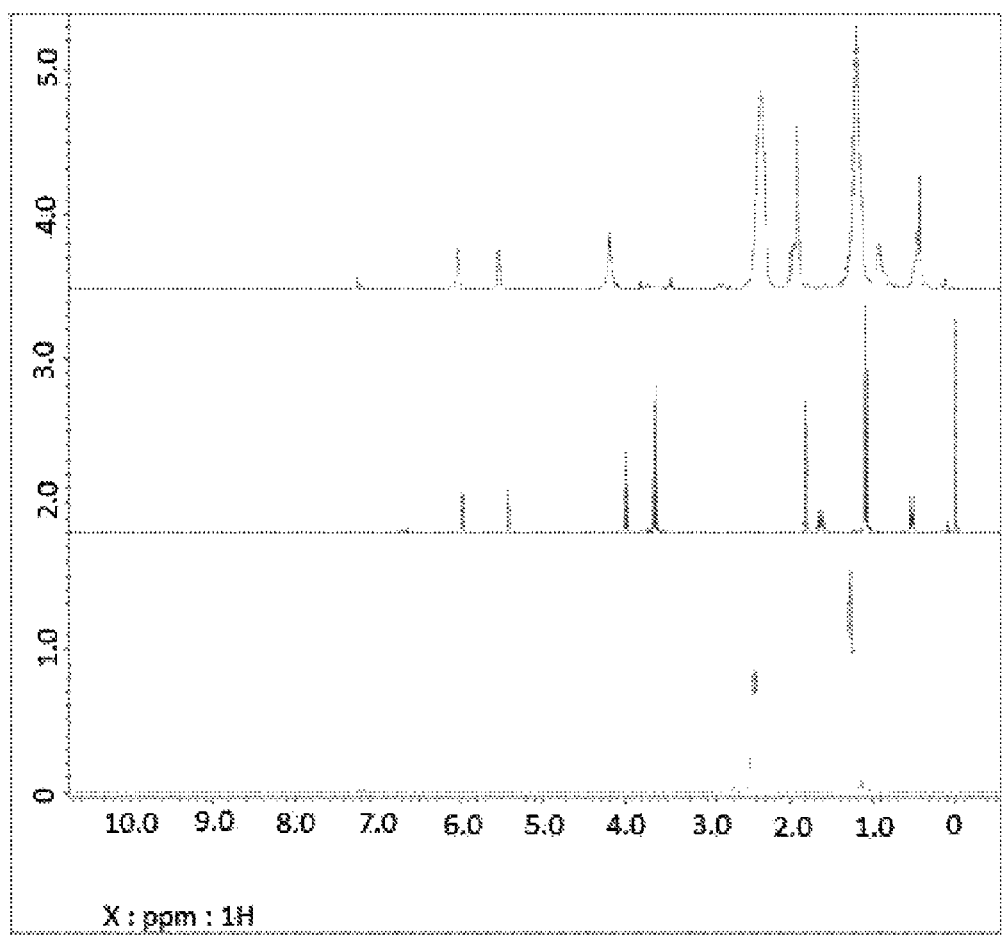
FIG. 1A is an analysis plot of $^1$H NMR analysis for the product of Example 2
FIG. 1B is an analysis plot of $^1$H NMR analysis for methacryloxypropylmethyldiethoxysilane starting material.
FIG. 1C is an analysis plot of $^1$H NMR analysis for 6/2 F-POSS.

As used herein, the term "long-chain fluorinated alkyl" means any straight chain or branched chain alkyl group having from 5 to 12 carbon atoms in the longest continuous chain of carbon atoms as counted from the point of attachment of the chain of carbon atoms to the silicon atom at any apex of the silicon-oxide core, where at least one hydrogen atom in the straight chain or branched chain alkyl group is replaced by a fluorine atom. Any number of hydrogen atoms in the straight chain or branched chain alkyl group can be replaced with fluorine atoms within the meaning of "long chain fluorinated alkyl" as used herein. For example, the terminal methyl group of a straight chain alkyl group having six carbon atoms in the chain (e.g. a hexyl group) can have each of the pendent hydrogen atoms replaced by a fluorine atom (e.g. a trifluoromethyl) to provide a long chain fluorinated alkyl group having the formula —CH$_2$CH$_2$CH$_2$CH$_2$CH$_2$CF$_3$. In another example, the last two carbon atoms of a straight chain alkyl group having six carbon atoms in the chain can have each of the pendent hydrogen atoms replaced by a fluorine atom (e.g. a trifluoroethyl) to provide a long chain fluorinated alkyl group having the formula —CH$_2$CH$_2$CH$_2$CH$_2$CF$_2$CF$_3$. This exemplary pattern can be continued to include within the definition of "long chain fluorinated alkyl" groups of the formula —CH$_2$CH$_2$CH$_2$CF$_2$CF$_2$CF$_3$, —CH$_2$CH$_2$CF$_2$CF$_2$CF$_2$CF$_3$, —CH$_2$CF$_2$CF$_2$CF$_2$CF$_2$CF$_3$, and —CF$_2$CF$_2$CF$_2$CF$_2$CF$_2$CF$_3$. As is commonly known in the art, an alkyl group where every hydrogen atoms in the chain is replaced by a fluorine atom is known as a "perfluorinated" alkyl group.

When less than all of the carbon atoms in the longest continuous chain of carbon atoms have hydrogens replaced by fluorine atoms, the "long chain fluorinated alkyl" group can be identified by the shorthand X/Y, where X is the number of terminal carbon atoms in the longest continuous chain of carbon atoms as counted from the point of attachment of the chain of carbon atoms to the silicon atom at any apex of the silicon-oxide core, and Y is the remaining number of carbon atoms in the longest continuous chain of carbon atoms on which hydrogen atoms are not replaced by fluorine atoms. For example, a long chain fluorinated alkyl group of the formula —CH$_2$CH$_2$CF$_2$CF$_2$CF$_2$CF$_3$ can be given the shorthand 4/2. Other exemplary long chain fluorinated alkyl groups include but are not limited to 3/3, 6/2, 4/4, 8/2, 6/4 and the like.

When the shorthand X/Y is used herein in connection with F-POSS, the name provided refers to the F-POSS molecule each of the groups attached to the apices of the silicon-oxide core is of the long chain fluorinated alkyl group type defined by the X/Y. For example, 6/2 F-POSS refers to an F-POSS molecule of Formula I, wherein each of the R groups at the apices of the silicon-oxide core is a 6/2 long chain fluorinated alkyl group as defined herein.

As used herein, "alkyl" refers to a saturated aliphatic hydrocarbon radical including straight chain and branched chain groups of 1 to 20 carbon atoms (e.g. $C_1$-$C_{20}$), preferably 1 to 12 carbon atoms (e.g. $C_1$-$C_{12}$), more preferably 1 to 8 carbon atoms (e.g. $C_1$-$C_8$), or 1 to 6 carbon atoms (e.g. $C_1$-$C_6$), or 1 to 4 carbon atoms (e.g. $C_1$-$C_4$). "Lower alkyl" refers specifically to an alkyl group with 1 to 4 carbon atoms. Examples of alkyl groups include methyl, ethyl, propyl, 2-propyl, n-butyl, iso-butyl, tert-butyl, pentyl, and the like. Alkyl may be substituted or unsubstituted. Typical substituent groups include those conventionally known in the art, such as cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring. Substituent groups also include those described elsewhere in this disclosure in connection with alkyl.

As used herein, "cycloaylkyl" refers to a 3 to 10 member all-carbon monocyclic ring ($C_3$-$C_{10}$), an all-carbon 5-member/6-member or 6-member/6-member fused bicyclic ring (a "fused" ring system means that each ring in the system shares an adjacent pair of carbon atoms with each other ring in the system) wherein one or more of the rings may contain one or more double bonds but none of the rings has a completely conjugated pi-electron system. "Cycloalkyl" includes 3 to 8 member all-carbon monocyclic ring (e.g. "$C_3$-$C_8$ cycloalkyl"), Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^x$R$^y$, with R$^x$ and R$^y$ as defined above. Substituent groups also include those described elsewhere in this disclosure in connection with cycloalkyl.

As used herein, "alkenyl" refers to an alkyl group, as defined herein, that is further defined by the inclusion of at least two carbon atoms and at least one carbon-carbon double bond. "Alkenyl" includes groups having from 2 to 8 carbon atoms and at least one carbon-carbon double bond (e.g. "C$_2$-C$_8$ alkenyl"). Representative examples include, but are not limited to, ethenyl, 1-propenyl, 2-propenyl, 1-, 2-, or 3-butenyl, and the like. Alkenyl may be substituted as described above for alkyl or unsubstituted. Substituent groups also include those described elsewhere in this disclosure in connection with alkenyl.

As used herein, "alkynyl" refers to an alkyl group, as defined herein, that is further defined by the inclusion of at least two carbon atoms and at least one carbon-carbon triple bond. "Alkynyl" includes groups having from 2 to 8 carbon atoms and at least one carbon-carbon triple bond (e.g. "C$_2$-C$_8$ alkynyl"). Representative examples include, but are not limited to, ethynyl, 1-propynyl, 2-propynyl, 1-, 2-, or 3-butynyl, and the like. Alkynyl may be substituted as described above for alkyl or unsubstituted. Substituent groups also include those described elsewhere in this disclosure in connection with alkynyl.

As used herein, "aryl" refers to an all-carbon monocyclic or fused-ring polycyclic groups of 6 to 14 carbon atoms (C$_6$-C$_{14}$) having a completely conjugated pi-electron system. Aryl includes all-carbon monocyclic or fused-ring polycyclic groups of 6 to 10 carbon atoms (e.g. "C$_6$-C$_{10}$ aryl"). Examples, without limitation, of aryl groups are phenyl, naphthalenyl and anthracenyl. The aryl group may be substituted as described above for alkyl or unsubstituted. Substituent groups also include those described elsewhere in this disclosure in connection with aryl.

As used herein, "heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. "Heteroaryl" includes groups as defined herein having from five to seven ring atoms (e.g. "5-7 membered heteroaryl"). Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted as described above for alkyl or unsubstituted. Substituent groups also include those described elsewhere in this disclosure in connection with heteroaryl.

As used herein, "heterocyclic" refers to a monocyclic or fused ring group having in the ring(s) of 3 to 12 ring atoms, in which one or two ring atoms are heteroatoms selected from N, O, and S(O)$_n$ (where n is 0, 1 or 2), the remaining ring atoms being C. The rings may also have one or more double bonds. However, the rings do not have a completely conjugated pi-electron system. "Heterocyclic" includes groups as defined herein having from five to seven ring atoms (e.g. "5-7 membered heterocyclic"). The heterocyclic group may be substituted as described above for alkyl or unsubstituted. Substituent groups also include those described elsewhere in this disclosure in connection with heterocyclic.

As used herein, "alkoxy" refers to both an —O-(alkyl) or an —O-(unsubstituted cycloalkyl) group. The alkoxy group may be substituted as described above for alkyl or unsubstituted. Substituent groups also include those described elsewhere in this disclosure in connection with alkoxy. Representative examples include, but are not limited to, methoxy, ethoxy, propoxy, butoxy, cyclopropyloxy, cyclobutyloxy, cyclopentyloxy, cyclohexyloxy, and the like.

DETAILED DESCRIPTION

Silsesquioxanes have a cage-like structure, which is most commonly a cube, hexagonal prism, octagonal prism, decagonal prism, or dodecagonal prism. In exemplary embodiments, of the various possible F-POSS cage molecular structures, the cube-like ("T8") cage structure is provided in connection with the invention. F-POSS molecules consist of a silicon-oxide core [SiO$_{1.5}$] with a periphery of long-chain fluorinated alkyl groups.

Provided herein are methods of producing derivatized F-POSS molecules. The process can be represented by the reaction scheme shown in scheme 1. The processes described herein generally involve contacting an F-POSS of the Formula I with a dialkoxysilane compound in the presence of a base catalyst to form the desired derivatized F-POSS of the Formula II.

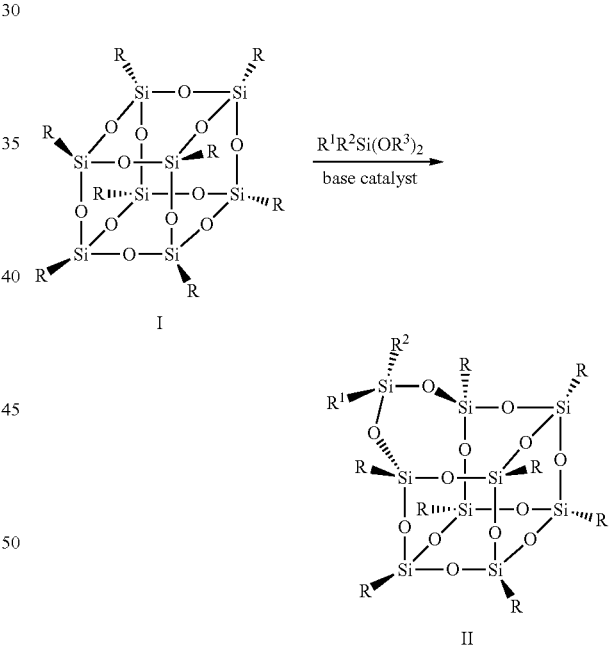

One of skill in the art will recognize that the dialkozysilane compound employed in connection with the processes described herein can be any dialkoxysilane known in the art. The identity of desired substituents R$^1$ and R$^2$ will vary greatly depending on what application the resulting derivatized F-POSS molecule will be used for. In some embodiments, the processes described herein provide a derivatized F-POSS molecule having a polymerizable group, such as an olefin, capable of reacting under free-radical polymerization conditions. For example, a derivatized F-POSS molecule having a methyl methacrylate (MMA) covalently bound to the silicon-oxide core can be produced by the processes described herein to provide a MMA F-POSS monomer capable of free radical polymerization with other monomers (e.g. methylmethacrylate).

In some embodiments, the processes described herein provide a derivatized F-POSS molecule having a polymerizable group, such as a strained cyclic olefin, capable of reacting under olefin metathesis polymerization conditions such as ring-opening metathesis polymerization (e.g. ROMP). For example, a derivatized F-POSS molecule having a strained cyclic olefin such as norbornene or cyclopentene covalently bound to the silicon-oxide core can be produced by the processes described herein to provide a cyclic olefin F-POSS monomer capable of polymerization with other monomers (e.g. cyclopentene) under ROMP conditions.

In some embodiments, the processes described herein provide a derivatized F-POSS molecule having a polymerizable group, such as an olefin, capable of reacting under reversible addition-fragmentation chain transfer conditions (e.g. RAFT). For example, a derivatized F-POSS molecule having a methyl methacrylate (MMA) covalently bound to the silicon-oxide core can be produced by the processes described herein to provide a MMA F-POSS monomer capable of free radical polymerization with other monomers (e.g. methylmethacrylate).

In some embodiments, the processes described herein provide a derivatized F-POSS molecule having a polymerizable group, such as an isocyanate, capable of reacting under conditions suitable for the formation of polyurethanes. For example, a derivatized F-POSS molecule having an arylisocyanate or a methyl diphenyl isocyanate (e.g. MDI) covalently bound to the silicon-oxide core can be produced by the processes described herein to provide a an isocyanate derivatized F-POSS monomer capable of reacting with polyols, chain extenders or cross-linkers to provide a polyurethane.

One of skill in the art will readily appreciate that the identity of the F-POSS molecule used in connection with the processes described herein is not of particular limitation. The F-POSS molecule can be any of those known in the art. For example, in some embodiments, F-POSS molecules of the type shown in Figure I where the long chain fluorinated alkyl group attached to the silicone-oxide core gives rise to a 6/2 F-POSS, a 4/2 F-POSS, a 8/2 F-POSS and the like. It will also be appreciated that in some embodiments, the processes described herein can be applied to so called "blended" F-POSS molecules of the Formula III

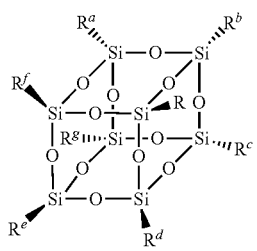

III where R, $R^a$, $R^b$, $R^c$, $R^d$, $R^e$, $R^f$ and $R^g$ can represent multiple different long chain fluorinated alkyl groups.

In exemplary embodiments, a blend of several distinct F-POSS molecules can be synthesized from a first feedstock fluorinated triethoxysilane and a second feedstock fluorinated triethoxysilane, each feedstock having a different long chain fluorinated alkyl group incorporated into the fluorinated triethoxysilane. The end product synthesized is a distribution of F-POSS molecules having portions made up of distinct F-POSS molecules with one of several R substituents (e.g., $R^a$, $R^b$, $R^c$, etc.). A portion of the F-POSS molecules have a matrix structure having all eight apices with a substituent $R^a$ and having the same long chain fluorinated alkyl group. A portion of the molecules will have all eight apices with a substituent $R^b$. Formula [5] below exemplifies a molecular formula of a blended F-POSS having (n)$R^a$ units and (8-n)$R^b$ units, where n is a number between 0 and 8.

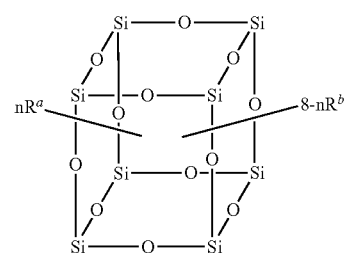

A portion of the molecules have a matrix structure in which one or more apices have a substituent $R^a$ and the remainder have a substituent $R^b$, where $R^a$ and $R^b$ represent different long chain fluorinated alkyl groups. In some embodiments, the blend of F-POSS molecules may form a Gaussian distribution of F-POSS molecules having different ratios of $R^a$ and $R^b$. For example, in one exemplary embodiment, one portion of the blend may be made up of an F-POSS molecule with a molar ratio of $R^a:R^b=0:8$, in other words, all eight apices have $R^b$. Another portion may have a molar ratio of $R^a:R^b=1:7$, in other words, seven of the apices have $R^b$ and one apex has $R^a$. Another portion has a ratio of 2:6. And, other portions have ratios of 3:5, 4:4, 5:3, 6:2, 7:1 and 8:0. In exemplary embodiments, the distribution of $R^a:R^b$ ratios generally comprises a Gaussian distribution. In exemplary embodiments, the distribution of ratios can be predetermined to an extent, or tuned, based on reaction conditions and amounts used of each substituent. It will be appreciated that blended F-POSS molecules can be prepared from three or more feedstocks of fluorinated triethoxysilanes to yield a distribution of blended F-POSS molecules having constituent long chain fluorinated alkyl groups distributed in varying degrees according the to number of feedstock inputs.

It will be appreciated that the base catalyst for use in connection with the present disclosed process can be of wide variation. For example, the aqueous base catalyst used in connection with the processes described herein can be alkyl or aryl quaternary ammonium catalysts, such as tetrabutyl ammonium hydroxide, tetrabenzyl ammonium hydroxide and alternate counter-ions thereof such as phosphate, carbonate, sulfate, fluoride, and the like; alkoxide bases, such as potassium t-butoxide, sodium ethoxide; inorganic bases such as KOH, NaOH, $K_2CO3$, $Cs_2CO_3$, sodium acetate, potassium iodide (KI), potassium fluoride (KF), cesium fluoride (CsF), magnesium oxide (MgO), and the like; organic bases such as triethylamine, diisopropyl ethylamine, triethanolamine, 1,8-Diazabicyclo[5.4.0]undec-7-ene (DBU), and the like; lithium bases, such as n-BuLi, t-BuLi and other organic anions; bis(trimethylsilyl)amine bases, such as NaHMDS, KHMDS, and LiHMDS; and phosphazene bases. In some embodiments, the aqueous base catalyst can be a alkyl or aryl quaternary ammonium catalysts, such as tetrabutyl ammonium hydroxide, tetrabenzyl ammonium hydroxide and alternate counter-ions thereof such as phosphate, carbonate, sulfate and fluoride. In some embodiments, the aqueous base catalyst can be a tetrabutyl ammonium hydroxide, such as tetraethylammonium hydroxide, tetrabutylammonium hydroxide, and the like.

The processes of the present disclosure can be described as embodiments in any of the following numbered clauses. It will be understood that any of the embodiments described herein can be used in connection with any other embodiments described herein to the extent that the embodiments do not contradict one another.

1. A process for preparing a derivatized F-POSS of the formula

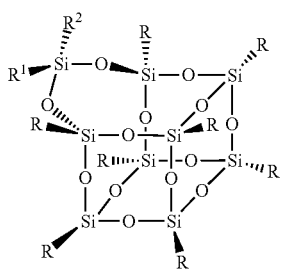

II comprising the step of contacting at least one F-POSS molecule of the formula

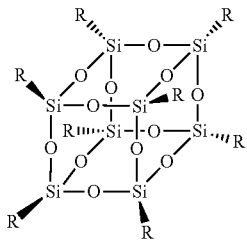

I with a compound of the formula $R^1R^2Si(OR^3)_2$,
wherein
R is a long chain fluorinated alkyl;
$R^1$ and $R^2$ are each independently selected from the group consisting of $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^1$ and $R^2$ is independently optionally substituted by an $R^4$;
$R^3$ is a $C_1$-$C_8$ alkoxy;
each $R^4$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^5$, —$NR^5R^6$, —OC(O)$R^5$, —C(O)O$R^5$, —C(O)$R^5$, —OC(O)O$R^5$, —C(O)NR^5R^6$, —OC(O)NR^5R^6$, —NR^5C(O)R^6$, —NR^5C(O)OR^6$ and —NR^5C(O)NR^5R^6$, and when $R^4$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^4$ is independently optionally substituted by an $R^7$;

each $R^5$ and $R^6$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, and 5-7 membered heteroaryl, wherein each hydrogen atom in $R^5$ and $R^6$ is independently optionally substituted by an $R^7$;
each $R^7$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^8$, —$NR^8R^9$, —OC(O)$R^8$, —C(O)O$R^8$, —C(O)$R^8$, —OC(O)O$R^8$, —C(O)NR^8R^9$, —OC(O)NR^8R^9$, —NR^8C(O)R^9$, —NR^8C(O)OR^9$ and —NR^8C(O)NR^8R^9$, and when $R^7$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^7$ is independently optionally substituted by an $R_{10}$;
each $R^8$ and $R^9$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^8$ and $R^9$ is independently optionally substituted by one or more $R^{10}$;
each $R^{10}$ is independently selected from the group consisting of hydrogen, halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^{11}$, —$NR^{11}R^{12}$, —OC(O)$R^{11}$, —C(O)O$R^{11}$, —C(O)$R^{11}$, —OC(O)O$R^{11}$, —C(O)NR^{11}R^{12}$, —OC(O)NR^{11}R^{12}$, —NR^{11}C(O)R^{12}$, —NR^{11}C(O)OR^{12}$ and —NR^{11}C(O)NR^{11}R^{12}$, and when $R^{10}$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, $C_3$-$C_8$ cycloalkyl or 5-7 membered heteroaryl, each hydrogen in $R^{10}$ is independently optionally substituted by a moiety selected from the group consisting of halo, —NCO, —$OR^{11}$, —$NR^{11}R^{12}$, —OC(O)$R^{11}$, —C(O)O$R^{11}$, —C(O)$R^{11}$, —OC(O)O$R^{11}$, —C(O)NR^{11}R^{12}$, —OC(O)NR^{11}R^{12}$, —NR^{11}C(O)R^{12}$, —NR^{11}C(O)OR^{12}$ and —NR^{11}C(O)NR^{11}R^{12}$; and
each $R^{11}$ and $R^{12}$ is independently selected from the group consisting of H, $C_1$-$C_8$ alkyl, $C_2$-$C_8$ alkenyl and $C_2$-$C_8$ alkynyl, and when $R^{11}$ or $R^{12}$ are $C_1$-$C_8$ alkyl, $C_2$-$C_8$ alkenyl or $C_2$-$C_8$ alkynyl, each hydrogen atom in $R^{11}$ and $R^{12}$ is independently optionally substituted by a fluorine atom,
in the presence of an aqueous base catalyst.

2. The process of clause 1, where $R^1$ is $C_1$-$C_8$ alkyl, wherein each hydrogen atom in $R^1$ is independently optionally substituted by an $R^4$.

3. The process of clause 1 or 2, wherein $R^4$ is —NCO, —$OR^5$, —OC(O)$R^5$, —C(O)O$R^5$, —C(O)$R^5$ or —OC(O)O$R^5$.

4. The process of any of the preceding clauses, wherein $R^5$ is $C_1$-$C_8$ alkyl, wherein each hydrogen atom in $R^5$ is independently optionally substituted by an $R^7$.

5. The process of any of the preceding clauses, wherein $R^5$ is $C_2$-$C_8$ alkenyl, wherein each hydrogen atom in $R^5$ is independently optionally substituted by an $R^7$.

6. The process of any of the preceding clauses, wherein $R^7$ is $C_1$-$C_8$ alkyl, —NCO, —$OR^8$, —$NR^8R^9$, —OC(O)$R^8$, —C(O)O$R^8$, —C(O)$R^8$ or —OC(O)O$R^8$.

7. The process of any of the preceding clauses, wherein $R^8$ is $C_1$-$C_8$ alkyl, $C_2$-$C_8$ alkenyl, $C_2$-$C_8$ alkynyl, $C_6$-$C_{10}$ aryl or 5-7 membered heteroaryl, wherein each hydrogen atom in $R^8$ is independently optionally substituted by one or more $R^{10}$.

8. The process of any of the preceding clauses, wherein $R^{10}$ is hydrogen or $C_1$-$C_8$ alkyl, and when $R^{10}$ is $C_1$-$C_8$ alkyl, $R^{10}$ is optionally substituted by a —OC(O)$R^{11}$.

9. The process of any of the preceding clauses, wherein $R^{11}$ is H or $C_1$-$C_8$ alkyl, and when $R^{11}$ is $C_1$-$C_8$ alkyl, each hydrogen atom in $R^{11}$ is independently optionally substituted by a fluorine atom.

10. The process of any of the preceding clauses, wherein $R^1$ is n-propyl, optionally substituted by an $R^4$.

11. The process of any of the preceding clauses, wherein $R^4$ is —OC(O)$R^5$ or —OC(O)O$R^5$.

12. The process of any of the preceding clauses, wherein $R^5$ is n-propyl, optionally substituted by an $R^7$.

13. The process of any of the preceding clauses, wherein $R^5$ is —CH=CH$_2$, optionally substituted by an $R^7$.

14. The process of clause 13, wherein $R^7$ is $C_1$-$C_8$ alkyl.

15. The process of clause 14, wherein $R^7$ is methyl.

16. The process of any of clauses 1 to 12, wherein $R^7$ is —OC(O)$R^8$ or —C(O)O$R^8$.

17. The process of any one of clauses 1 to 12 or 16, wherein $R^8$ is —CH=CH$_2$, optionally substituted by an $R^{10}$.

18. The process of clause 17, wherein $R^{10}$ is $C_1$-$C_8$ alkyl.

19. The process of clause 18, wherein $R^{10}$ is methyl.

20. The process of clause 1, wherein $R^1$ is $C_6$-$C_{10}$ aryl, wherein each hydrogen atom in $R^1$ is independently optionally substituted by an $R^4$.

21. The process of clause 1 or 20, wherein $R^4$ is $C_1$-$C_8$ alkyl, $C_2$-$C_8$ alkenyl or —NCO, and when $R^4$ is $C_1$-$C_8$ alkyl or $C_2$-$C_8$ alkenyl, each hydrogen atom in $R^4$ is independently optionally substituted by an $R^7$.

22. The process of clause 21, wherein $R^4$ is $C_2$-$C_8$ alkenyl, optionally substituted by an $R^7$.

23. The process of clause 21 or 22, wherein $R^4$ is —CH=CH$_2$, optionally substituted by an $R^7$.

24. The process of any one of clauses 21 to 23, wherein $R^7$ is methyl.

25. The process of clause 21, wherein $R^4$ is $C_1$-$C_8$ alkyl, optionally substituted by an $R^7$.

26. The process of clause 21 or 25, wherein $R^7$ is $C_6$-$C_{10}$ aryl, optionally substituted by an $R^{10}$.

27. The process of any one of clauses 21, 25 or 26, wherein $R^{10}$ is $C_2$-$C_8$ alkenyl or —NCO, and when $R^{10}$ is $C_2$-$C_8$ alkenyl, $R^{10}$ is optionally substituted by a moiety selected from the group consisting of halo, —NCO, —O$R^{11}$, —N$R^{11}R^{12}$, —OC(O)$R^{11}$, —C(O)O$R^{11}$, —C(O)$R^{11}$, —OC(O)O$R^{11}$, —C(O)N$R^{11}R^{12}$, —OC(O)N$R^{11}R^{12}$, —N$R^{11}$C(O)$R^{12}$, —N$R^{11}$C(O)O$R^{12}$ and —N$R^{11}$C(O)N$R^{11}R^{12}$.

28. The process of clause 27, wherein $R^{10}$ is —CH=CH$_2$.

29. The process of clause 27, wherein $R^{10}$ is —NCO.

30. The process of clause 1, wherein $R^1$ is $C_2$-$C_8$ alkenyl, wherein each hydrogen atom in $R^1$ is independently optionally substituted by an $R^4$.

31. The process of clause 30, wherein $R^4$ is halo.

32. The process of any one of the preceding clauses, wherein the aqueous base catalyst is an aqueous ammonium salt.

33. The process of any one of the preceding clauses, wherein the aqueous base catalyst is a tetraethylammonium salt.

34. The process of any one of the preceding clauses, wherein the aqueous base catalyst is tetraethylammonium hydroxide.

35. The process of any one of the preceding clauses, wherein the long chain fluorinated alkyl is 8/2, 6/2 or 4/2.

36. The process of any one of the preceding clauses, wherein the at least one F-POSS molecule is selected from the group consisting of 8/2 F-POSS, 6/2 F-POSS and 4/2 F-POSS.

37. The process of any one of the preceding clauses, wherein the at least one F-POSS molecule is 6/2 F-POSS.

38. The process of any one of the preceding clauses, wherein the at least one F-POSS molecule is 4/2 F-POSS.

39. The process of any one of the preceding clauses, wherein the long chain fluorinated alkyl is 6/2.

40. The process of any one of the preceding clauses, wherein the long chain fluorinated alkyl is 4/2.

41. The process of any one of the preceding clauses, wherein $R^2$ is $C_1$-$C_8$ alkyl.

42. The process of any one of the preceding clauses, wherein $R^2$ is methyl.

EXAMPLES

Materials

6/2 fluorinated polyhedral oligomeric silsequioxane, aka 6/2 F-POSS was obtained from Prime Organics. Methacryloxypropylmethyldiethoxy silane, 95%, was obtained from Gelest (SIM6486.8-50G, lot 7D-10507). Tetraethylammonium hydroxide in water was obtained from Acros Organics (Code 420291000, lot A0322694). Hexafluorobenzene was obtained from Aldrich (H8706-100G, lot MKBS2573V). Diethyl ether was obtained from Acros Organics (61508-5000, lot B0527523). 2,2'-Azobis(2-methylpropionitrile), 98%, was obtained from Sigma-Aldrich. 1H, 1H, 2H, 2H perfluorooctyltriethoxysilane was obtained from Sigma Aldrich (667420-25g). 1H, 1H, 2H, 2H-Nonafluorohexyltriethoxysilane was obtained from TCI America (T2860).

Example 1

Preparation of Methacryloxypropylmethyl 6/2 F-POSS 0.1 mmol (0.32 g) of 6/2 F-POSS and 0.1 mmol of methacryloxypropylmethyldiethoxy silane were added to an unsealed reaction vessel. A catalytic amount (~40 μL) of a 25% solution of tetraethylammonium hydroxide in water was added to the vessel. The vessel was heated to 127° C. with stirring for 1.5 hours. The vessel was cooled to ambient temperature and the contents diluted with ~1 mL of hexafluorobenzene. A clear solution resulted upon dilution with hexafluorobenzene. $^{29}$Si and $^1$H NMR were run using chloroform-d (CDCl$_3$) as the internal standard on a JEOL Eclipse$^+$ AS400 NMR. The $^{29}$Si and $^1$H NMR were consistent with the literature indicating the presence of the desired product.

Example 2

Preparation of Methacryloxypropylmethyl 6/2 F-POSS

The reaction described in Example 1 was repeated using 8.3×10$^{-4}$ mol (2.5 g) of 6/2 F-POSS in a 1:1 molar ratio with methacryloxypropylmethyldiethoxysilane (0.216 g) using a catalytic amount (0.124 g) of 25% tetraethylammonium hydroxide. The reaction vessel was heated to 127° C. for 1.5 hours with stirring then cooled to ambient temperature. $^{29}$Si and $^1$H NMR was run using CDCl$_3$ as the internal standard on a JEOL Eclipse$^+$ AS400 NMR. The reaction mixture was diluted with 10 mL of hexafluorobenzene and washed successively with 10 mL of water and 10 mL of saturated brine then dried over sodium sulfate and filtered. The solution was diluted with 90 mL of ethyl acetate and allowed to stand at ambient temperature for ~10 minutes, at which time a small amount of insoluble oil settled to the bottom. The supernatant liquid was decanted off and concentrated under reduced pressure to a sticky semi-solid material. The residue was taken up in 20 mL of diethyl ether and allowed to stand at ambient temperature for ~20 minutes. The precipitated solid material was collected by decanting off the supernatant ether layer. This solid was determined to be 6/2 F-POSS starting material by $^{29}$Si and $^1$H NMR (~350 mg collected). The remaining fines in the ether solution were filtered by syringing through a 5μ nylon frit. The solution was concentrated to half the volume and cooled to ~10° C.; however crystallization could not be induced. The solvent was removed under reduced pressure to give a viscous, semi-solid, thick material. $^{29}$Si NMR was consistent with the desired product. $^1$H NMR was consistent with the $^{29}$Si NMR indicating the correct ratio of vinyl to F-POSS methylene protons. $^1$H NMR is shown in FIG. 1A depicting the product, FIG. 1B depicting methacryloxypropylmethyldiethoxysilane starting material and FIG. 1C depicting 6/2 F-POSS.

Example 3

Preparation of Methacryloxypropylmethyl 6/2 F-POSS (Scale-Up)

The reaction described in Example 1 was scaled up using 0.007 mol (21 g) of 6/2 F-POSS in a 1:1 molar ratio with methacryloxypropylmethyldiethoxysilane (1.815 g) using a catalytic amount (1.04 g) of 25% tetraethylammonium hydroxide. The reaction vessel was heated to 127° C. for 1.5 hours with stirring then cooled to ambient temperature. $^{29}$Si and $^1$H NMR was run using CDCl$_3$ as the internal standard on a JEOL Eclipse$^+$ AS400 NMR to confirm that the desired product was present. The reaction mixture was diluted with 60 mL of hexafluorobenzene and washed successively with 60 mL of water and 60 mL of saturated brine then dried over sodium sulfate and filtered. The solution was diluted with 400 mL of ethyl acetate and allowed to stand at ambient temperature for ~10 minutes, at which time a small amount of insoluble oil settled to the bottom. The supernatant liquid was decanted off and concentrated under reduced pressure to a sticky semi-solid material. The residue was taken up in 250 mL of diethyl ether and allowed to stand at ambient temperature for ~20 minutes. The precipitated solid material was collected by decanting off the supernatant ether layer. The ether layer was concentrated under reduced pressure to an oily substance which was then treated with another 250 mL of diethyl ether. A small amount (~1 g) of material precipitated out of solution (NMR showed this material to be 6/2 F-POSS). The ether was decanted off and concentrated under reduced pressure. The residue was triturated once more with 250 mL of ether. The liquid was decanted from the solid, the ether solution was concentrated under reduced pressure and then concentrated two times with hexafluorobenzene as a co-solvent to remove the traces of diethyl ether. The yield was 17 g of material (80%).

Figure 2:
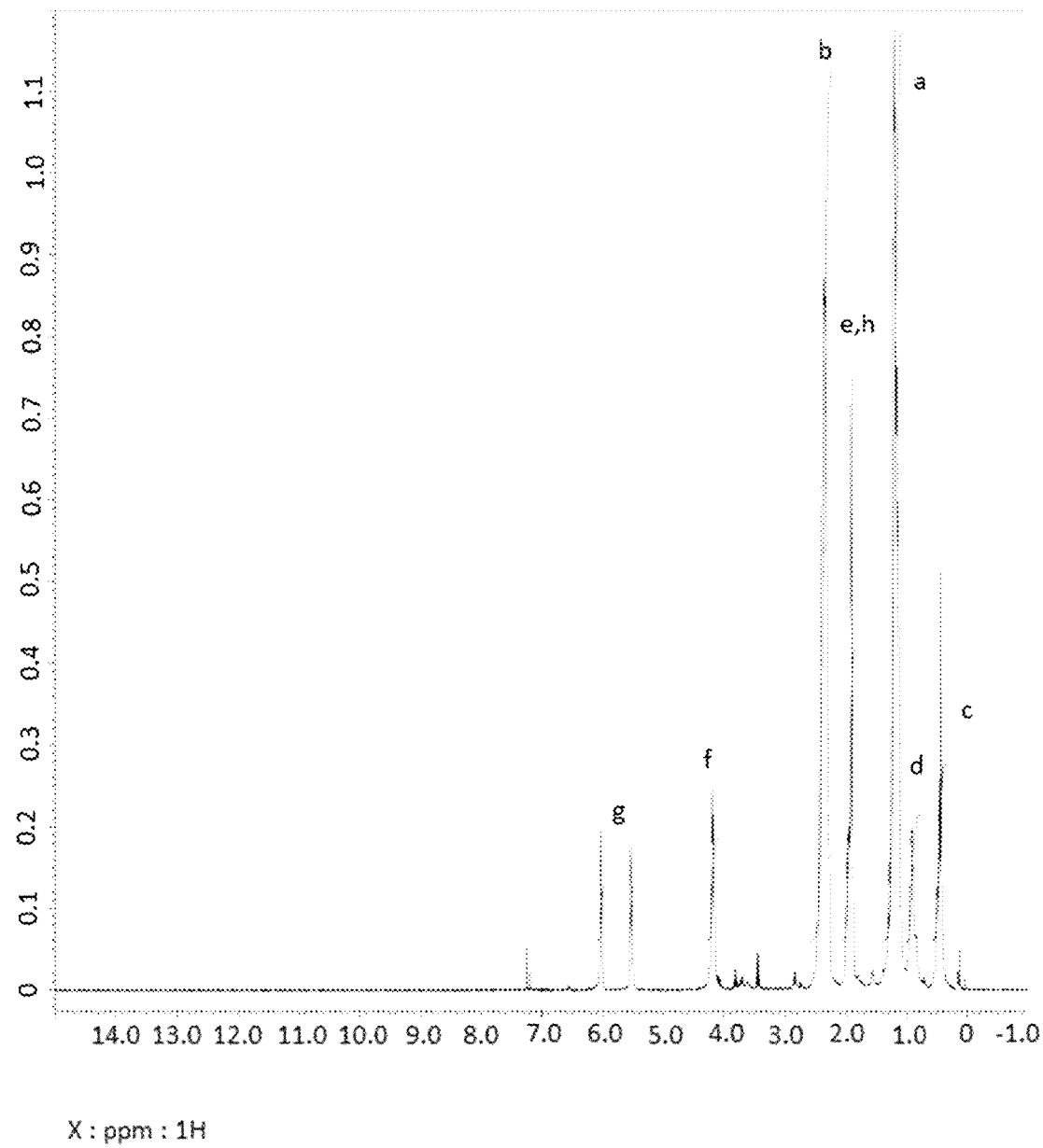
FIG. 2 is an analysis plot of $^1$H NMR analysis for methacryloxypropylmethyl 6/2 F-POSS according to Example 3.
Figure 3:
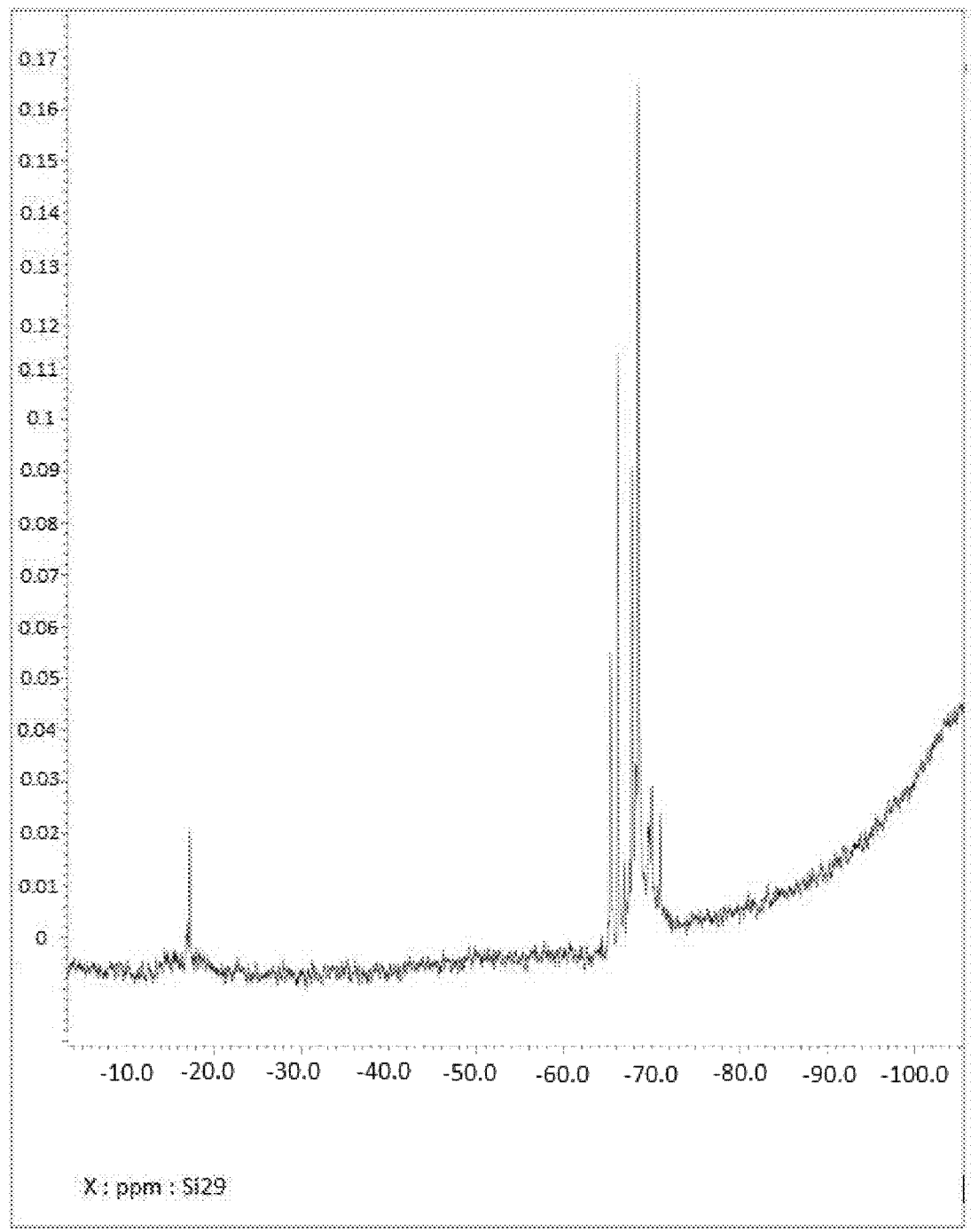
FIG. 3 is an analysis plot of $^{29}$Si NMR analysis for methacryloxypropylmethyl 6/2 F-POSS according to Example 3.

The $^{29}$Si and $^1$H NMR confirmed the presence of the desired product (see FIGS. 2 and 3). In addition the product was completely soluble in ether. The $^1$H NMR in hexafluorobenzene is consistent with the literature. Examination of the region around 0.46 ppm (the region for Si—CH$_3$) shows a reasonable doublet in approximately the same ratio as the doublet at −17 in the $^{29}$Si NMR. The peak observed at ~−17 ppm (see resonance at −17.27) on the $^{29}$Si NMR, indicates Si monomer insertion on F-POSS edge. Resonances between −65 and −70 ppm (see resonances at −65.26, −66.16, −67.8, −68.2, −68.49 and −70.0) are indicative of the F-POSS 6/2 cage and possibly corner insertion and/or cage rearrangement. The data suggests that there is roughly a 2:1 ratio of desired product to another material. Based on the proton NMR information and in conjunction with $^{29}$Si NMR, it is extremely likely that the other material (i.e. 8/2 or 10/2 FPOSS) has one unit of methacrylate monomer appended to it as well. Hence, the reaction appears to have yielded a mixture of the desired methacrylate 6/2 F-POSS monomer as well as a "rearranged" FPOSS with a single methacrylate attached. With reference to FIG. 2, the following resonance assignments were made for the desired product.

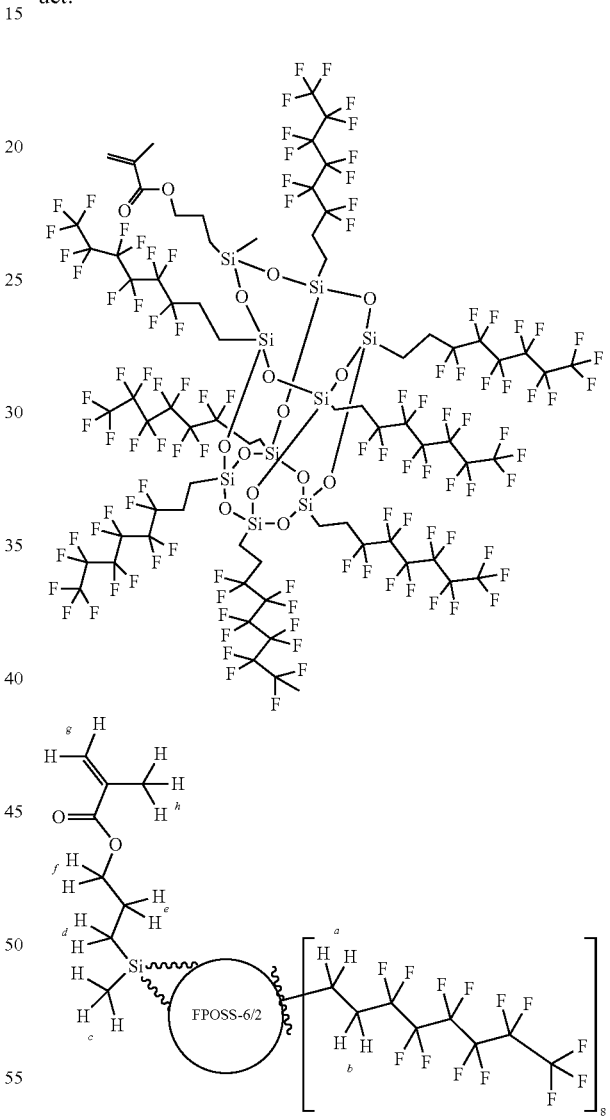

TABLE 1

| Resonance | Shift (δ, ppm) | H Integration |
|---|---|---|
| a | 1.15-1.23 | 16.05 |
| b | 2.35-2.37 | 15.35 |
| c | 0.433 | 3.14 |
| d | 0.90-1.00 | 2.25 |
| e + h | 1.92-1.95 | 5.11 |

TABLE 1-continued

| Resonance | Shift (δ, ppm) | H Integration |
|---|---|---|
| f | 4.18-4.22 | 1.85 |
| g | 6.02-6.03 | 0.97 |

Example 4

6/2 F-POSS-Methacrylate (6/2 F-POSS-MA)/Methylmethacrylate Polymer Synthesis Four separate comparison reactions were run under the same conditions with varying amounts of 6/2 F-POSS-MA.

Figure 4:
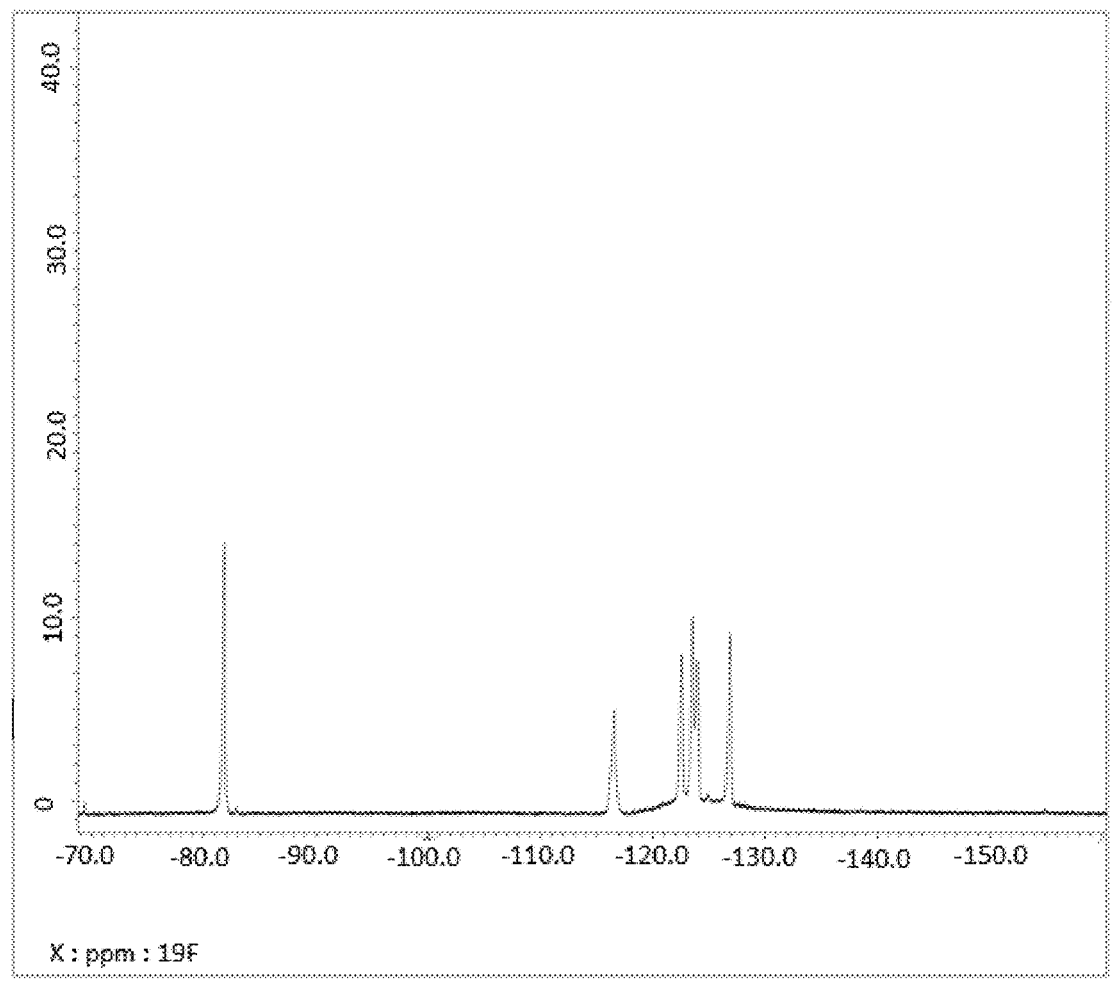
FIG. 4 is an analysis plot of $^{19}$F NMR 6/2 F-POSS-methacrylate (6/2 F-POSS-MA)/methylmethacrylate polymer according to Example 4 that showed 6 Fluorine peaks indicative of incorporation of FPOSS monomer into the MMA matrix.

A reaction vessel was charged with 25 mL of 4:1 hexafluorobenzene/THF and degassed for 20 minutes. To the vessel was added 6/2 F-POSS-MA monomer (either 0, 1, 5 or 10 weight percent), methylmethacrylate monomer (5 g total batch size) and 20 mg of 2,2'-azobis(2-methylpropionitrile) initiator. All reactions were run under nitrogen for 12 hours at 55° C. then 5 hours at 80° C. The reaction solution was poured into 150 mL of hexane and stirred with a spatula to break up the clumps. The solid material was filtered, washed thoroughly with hexane, and dried under high vacuum at 45° C. overnight. Polymer yields are shown in Table 2. Each polymer was determined to be soluble in Acetone, Methyl ethyl ketone, Tetrahydrofuran. The polymers were not soluble in Chloroform, Isopropanol. Characterization was performed on the 10% FPOSS-MA polymer. The $^1$H NMR was unremarkable but showed no vinyl protons; $^{19}$F NMR spectra showed 6 Fluorine peaks indicative of incorporation of FPOSS monomer into the MMA matrix (see FIG. 4, specifically resonances at −81.8, −116.55, −122.56, −123.53, −123.96 and −126.91).

Polymer Yields:

TABLE 2

| Reaction | Yield |
|---|---|
| 0% 6/2 F-POSS-MA monomer | 2.7 g |
| 1% 6/2 F-POSS-MA monomer | 2.0 g |
| 5% 6/2 F-POSS-MA monomer | 1.7 g |
| 10% 6/2 F-POSS-MA monomer | 1.55 g |

Example 5

Figure 5:
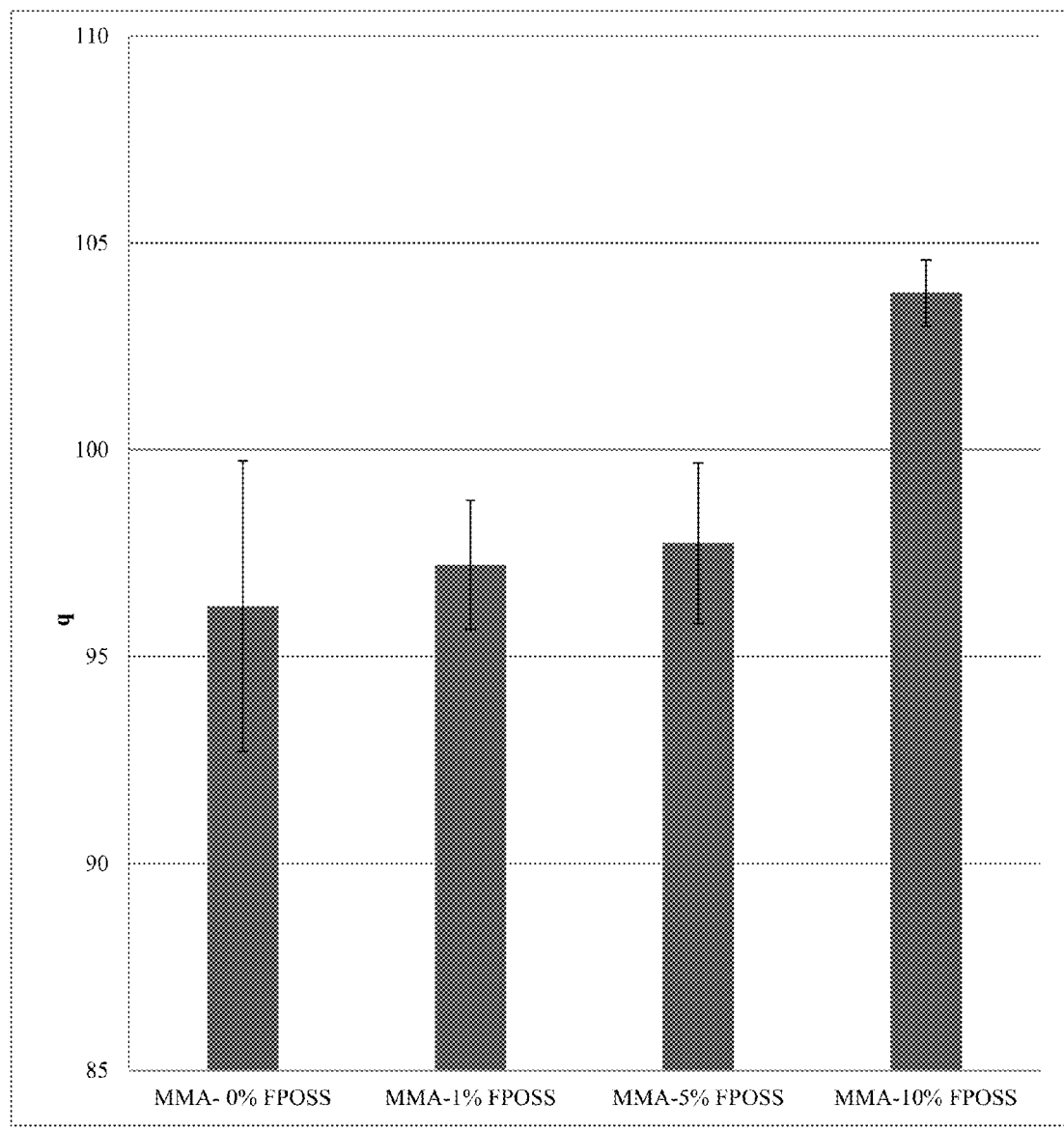
FIG. 5 is a graph of experiments showing the contact angle of water on 6/2 FPOSS-methylmethacrylate polymer on glass according to Example 5.
Figure 6:
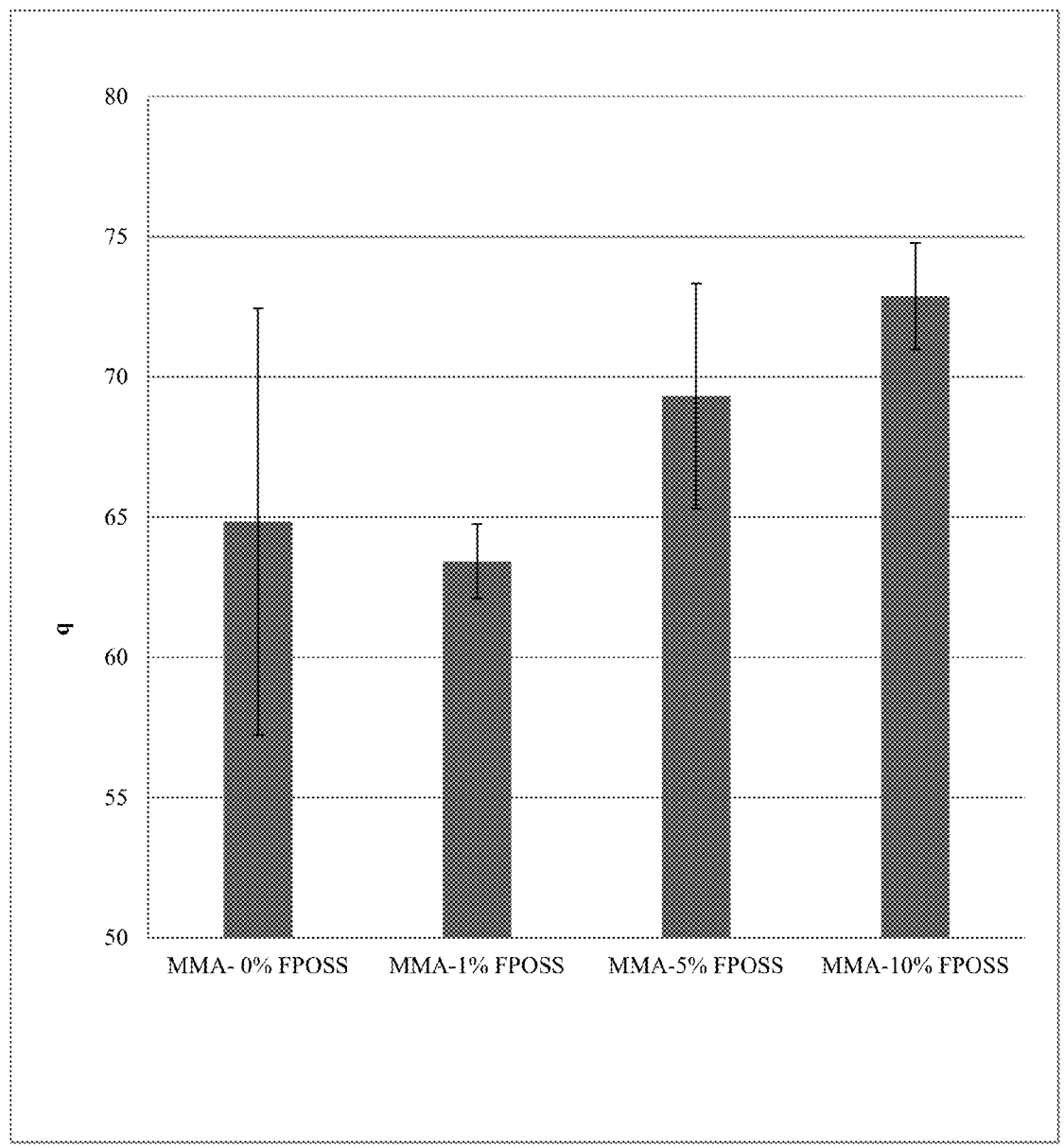
FIG. 6 is a graph of experiments showing the contact angle of hexadecane on 6/2 FPOSS-methylmethacrylate polymer on glass according to Example 5.

6/2 F-POSS-MA/Methylmethacrylate Polymer Contact Angle Measurements 50 mg of each polymer produced in Example 4 was dissolved in 600 uL of MEK (83.3 mg/mL). Each of the 6/2 F-POSS-MA polymers dissolved completely to a clear solution; the polymer containing 0% 6/2 F-POSS-MA remained a cloudy, milky solution. The polymer solutions (200 uL of each) were then coated on microscope slides by blade coating. Each 6/2 F-POSS-MA containing polymer coated to a clear film; the polymer containing 0% 6/2 F-POSS-MA did not coat well on glass becoming gel like and retracting on the glass. The coatings were dried overnight. Contact angle measurements of water and hexadecane were taken using a Kruss DSA100 drop shape analyzer (See FIGS. 5 and 6).

Example 6

1:3 Ratio of 1H, 1H, 2H, 2H Perfluorooctyltriethoxysilane:1H, 1H, 2H, 2H-Nonafluorohexyltriethoxysilane (Ratio of [25% 6/2]:[75% 4/2]), aka SB3 F-POSS 1.28 g of the 1H, 1H, 2H, 2H perfluorooctyltriethoxysilane and 3.1 g of 1H, 1H, 2H, 2H-nonafluorohexyltriethoxysilane (1:3 molar ratios) were taken in 10 mL ethanol, to which was added 0.3 mL of KOH solution (7.4 mg/mL). The mixture was stirred at room temperature for 24 h resulting in the precipitation of a white semi-solid product. The solvent in the reaction mixture was decanted, the precipitate washed repeatedly with ethanol, then dried under vacuum overnight at 45-50° C. The crude product was then dissolved in AsahiKlin AK-225G solvent, and then the organic layer washed three times with ddH$_2$O, dried over anhydrous magnesium sulfate, filtered, concentrated and dried under vacuum overnight at 80° C. The resulting purified product was still a semi-solid substance.

Figure 7:
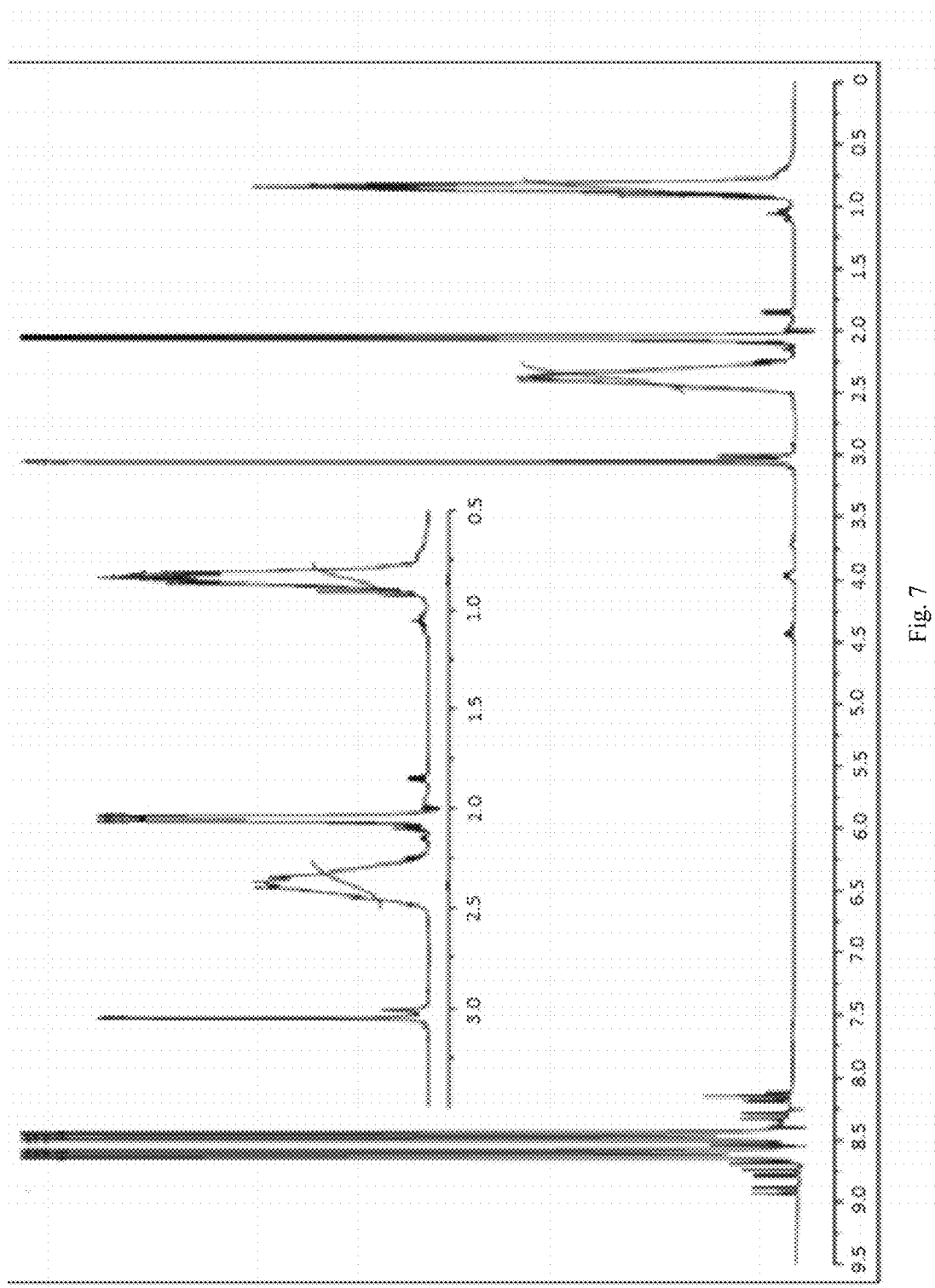
FIG. 7 is an analysis plot of $^1$H NMR analysis for a synthetic blend SB3 according to Example 6.

$^1$H NMR analysis for the synthetic blend SB3 F-POSS is shown in FIG. 7. $^1$H NMR in acetone-d$^6$ (with few drops of AK-225G) showed shifts at 2.45-2.34 ppm (m, 16H) and 0.91-0.80 (m, 16H), with slight impurity/precursor peaks between 4.5-3.5 ppm. This product was readily soluble in acetone+AK-225G (NMR solvent mixture), solubility being very similar to that of the 4/2 F-POSS.

Figure 8:
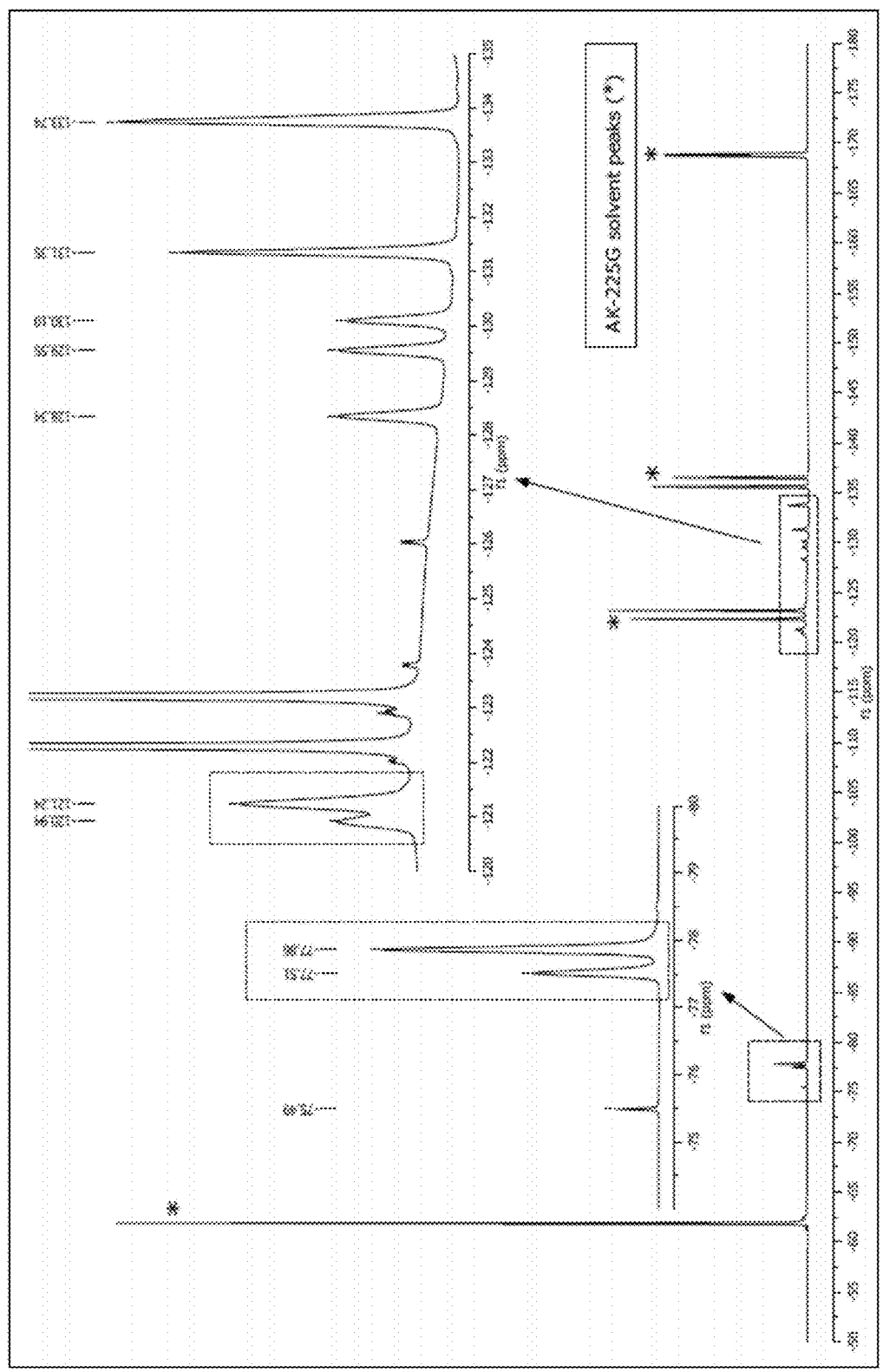
FIG. 8 is an analysis plot of $^{19}$F NMR analysis for the synthetic blend SB3 according to Example 6.

$^{19}$F NMR analysis for the synthetic blend SB3 F-POSS is shown in FIG. 8. $^{19}$F NMR spectrum for the synthetic blend SB3 showed the following chemical shifts: −77.51, −77.86, −120.94, −121.24, −128.34, −129.55, −130.10, −131.35 and −133.74. Using the spectrum for the 50/50 synthetic blend as a reference, peak assignments can be made for —CF$_2$— and —CF$_3$ groups for the two different side chains in the 75/25 blend:

Peaks from 4/2 side chain: δ −77.86 (for —CF$_3$), −121.24 (for —CF$_2$—), −131.35 (for —CF$_2$—) and −133.74 (for —CF$_2$—) Peaks from 6/2 side chain: δ 77.51 (for —CF$_3$), −120.94 (for —CF$_2$—), −128.34 (for —CF$_2$—), −129.55 (for —CF$_2$—), −130.10 (for —CF$_2$—) and −133.74 (for —CF$_2$—, overlapped with the 4/2 side chain) Interestingly, as highlighted by the rectangular boxes in the figure above, the peak height for that at −77.51 ppm (—CF$_3$ from 6/2 side chain) is smaller than that at −77.86 ppm (—CF$_3$ from 4/2 side chain). Incidentally, these two peak heights and integrations were almost 1:1 in the 50/50 blend. A similar trend is observed for the peak heights at −120.94 ppm (from 6/2 side chain) and −121.24 (from 4/2 side chain).

Figure 9:
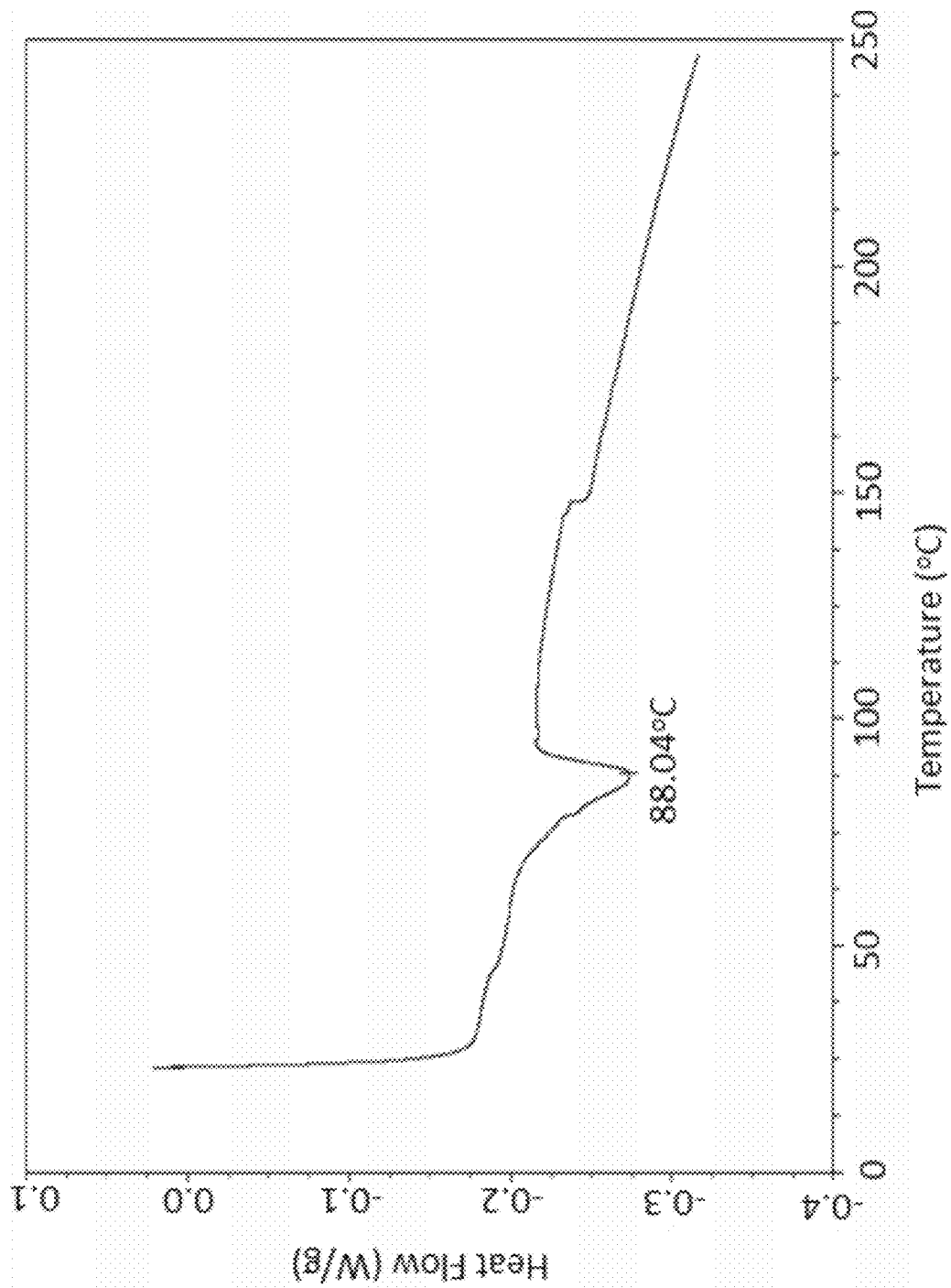
FIG. 9 is a graph of a first Differential Scanning calorimetry analysis of SB3 prepared according to Example 6.
Figure 10:
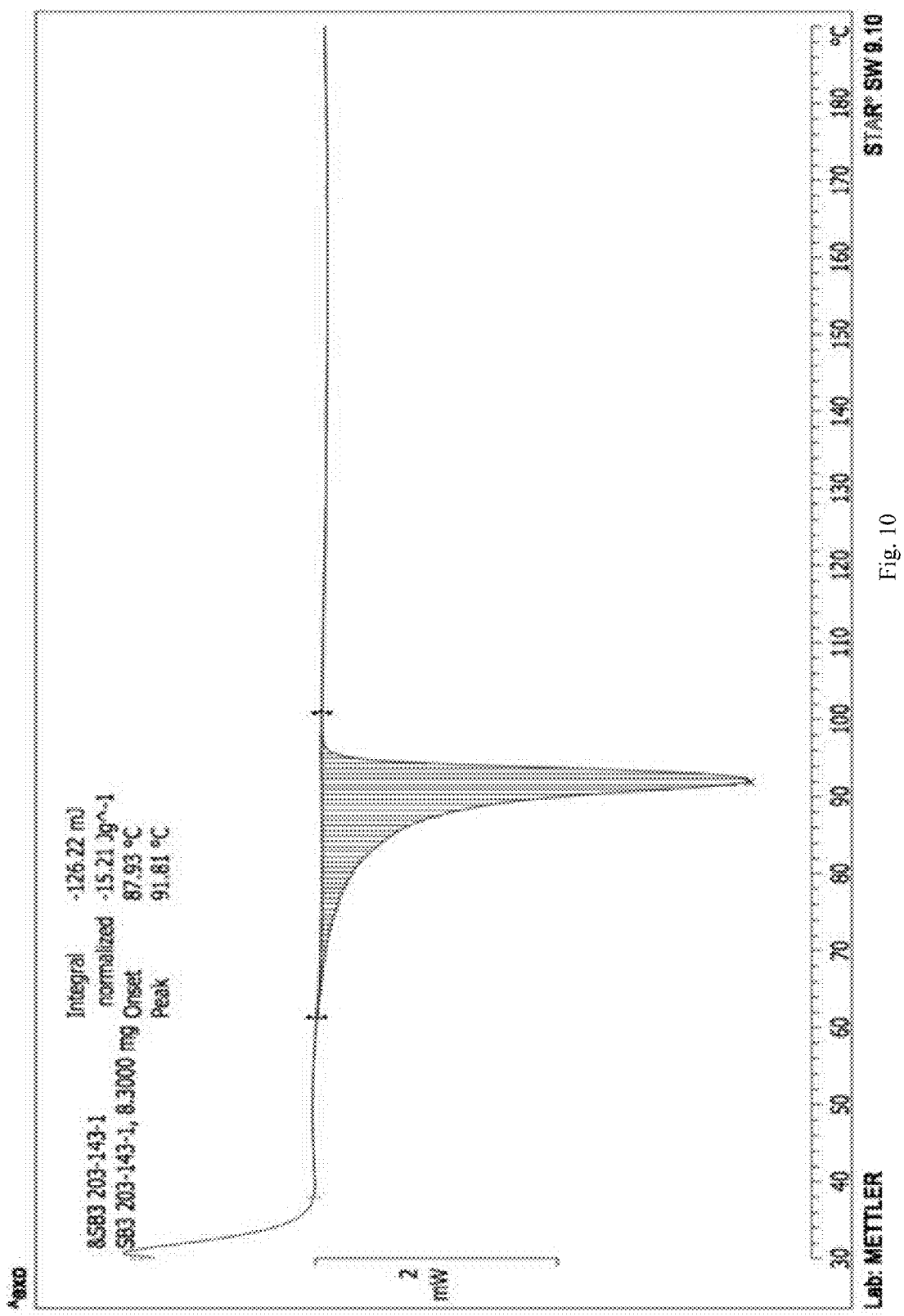
FIG. 10 is a graph of a second Differential Scanning calorimetry analysis of SB3 prepared according to Example 6.

DSC of SB3 F-POSS is shown in FIGS. 9 and 10. The melting points of pure 4/2 and 6/2 F-POSS are about 30° C. higher than those of the synthetic blend SB3 F-POSS. The fact that the melting points of the synthetic blend F-POSS are different suggests that different compounds with different properties were chemically formed by varying the molar ratios of the precursors.

Example 7

SB3 F-POSS Methacrylate Monomer Synthesis (SB3 F-POSS-MA)

The reaction of SB3 F-POSS in a 1:1 molar ratio with methacryloxypropylmethyl-diethoxysilane using a catalytic amount of 25% tetraethylammonium hydroxide was performed by combining the reagents into a reaction vessel, heating to 127° C. for 1.5 hours with stirring then cooling to ambient temperature. The reaction mixture was diluted with 30 mL of hexafluorobenzene and washed successively with 30 mL of water and 30 mL of saturated brine, dried over sodium sulfate, and filtered. The filtrate was concentrated under reduced pressure to a thick viscous liquid. The residue was taken up in 200 mL of ether and allowed to stand at ambient temperature for ~20 minutes. Only minimal precipitate formed. The precipitated solid material was collected by decanting off the supernatant ether layer. The ether layer was concentrated under reduced pressure to a clear viscous oil that was dried overnight at 40° C. under high vacuum. The yield was ~3.5 g of SB3 F-POSS-MA.

Figure 11:
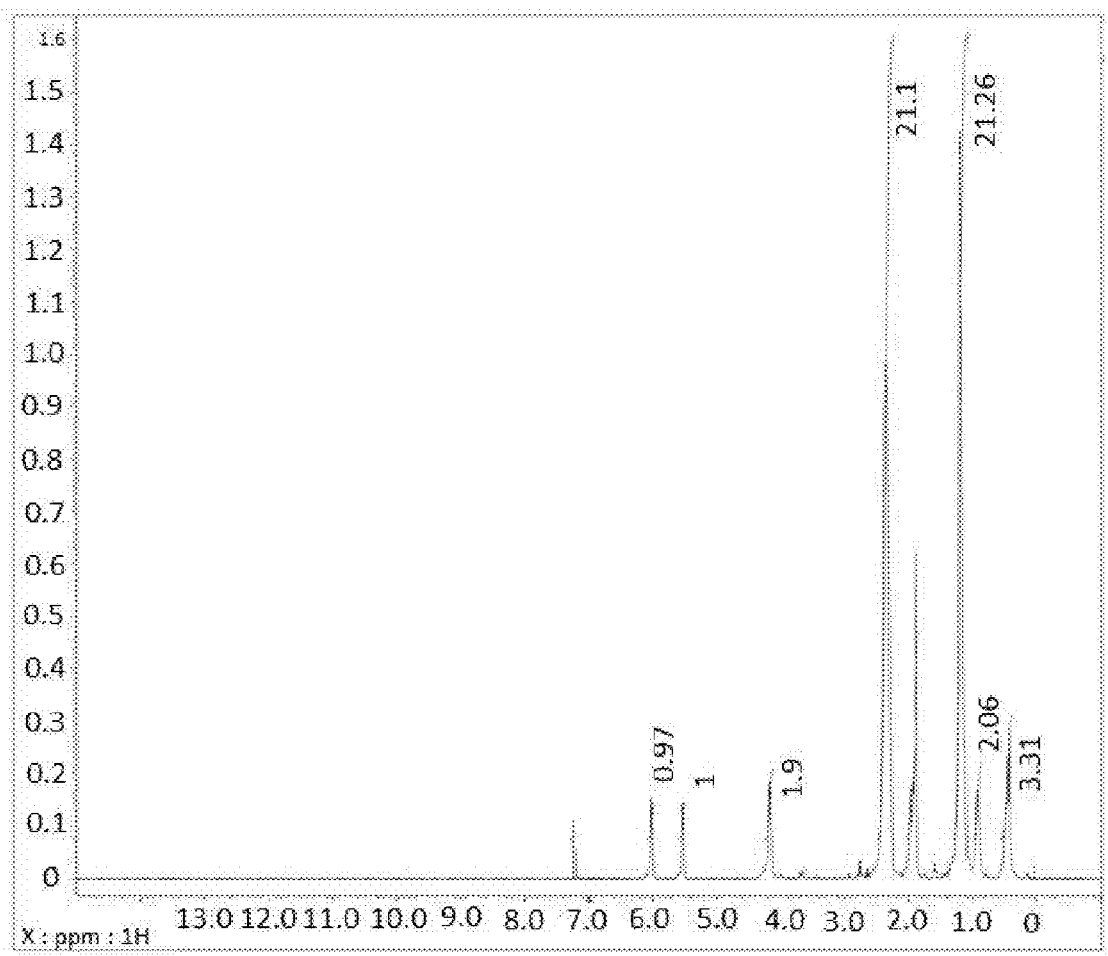
FIG. 11 is an analysis plot of $^1$H NMR analysis for SB3 F-POSS methacrylate monomer according to Example 7.
Figure 12:
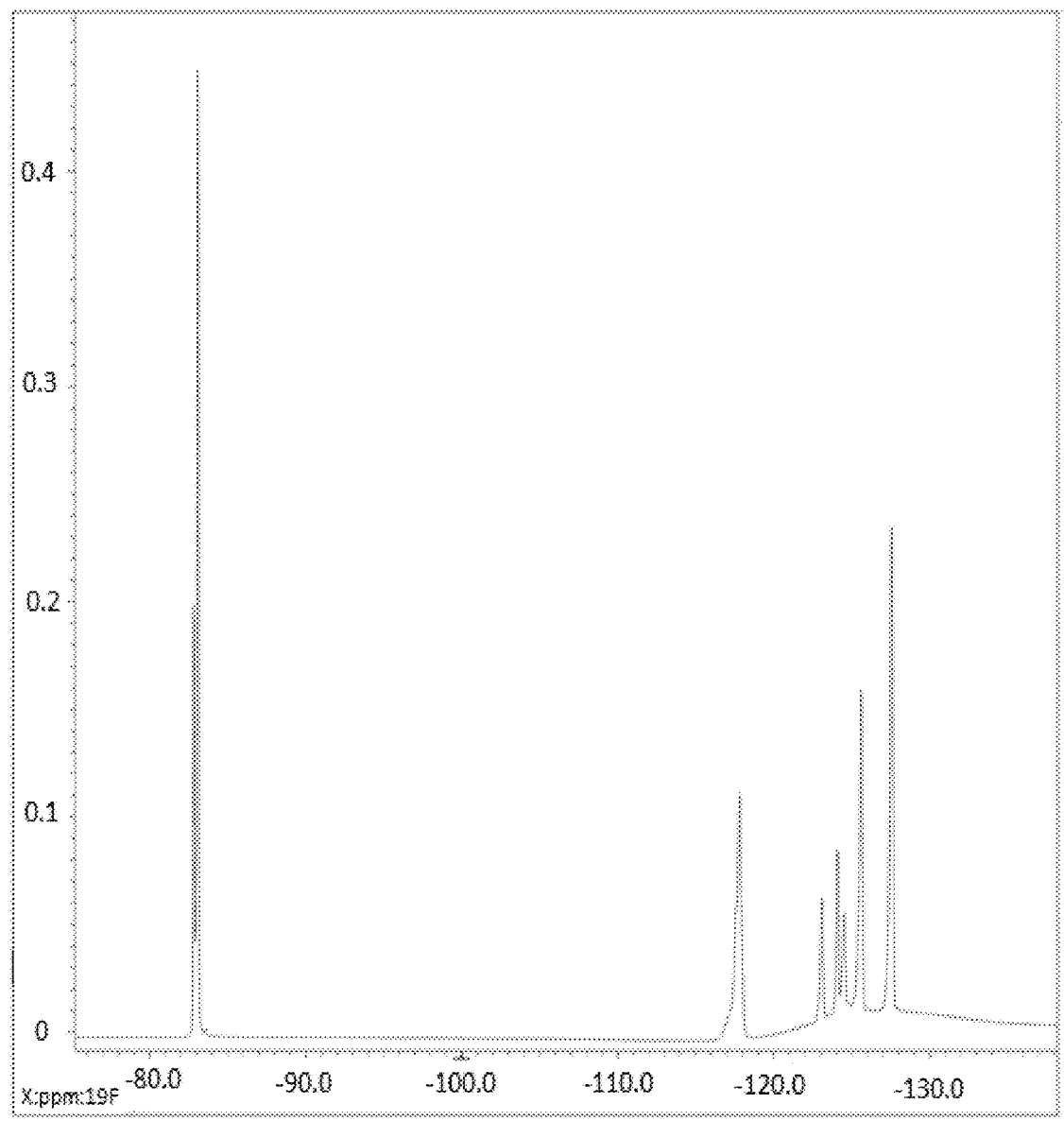
FIG. 12 is an analysis plot of $^{19}$F NMR analysis for SB3 F-POSS methacrylate monomer according to Example 7.
Figure 13:
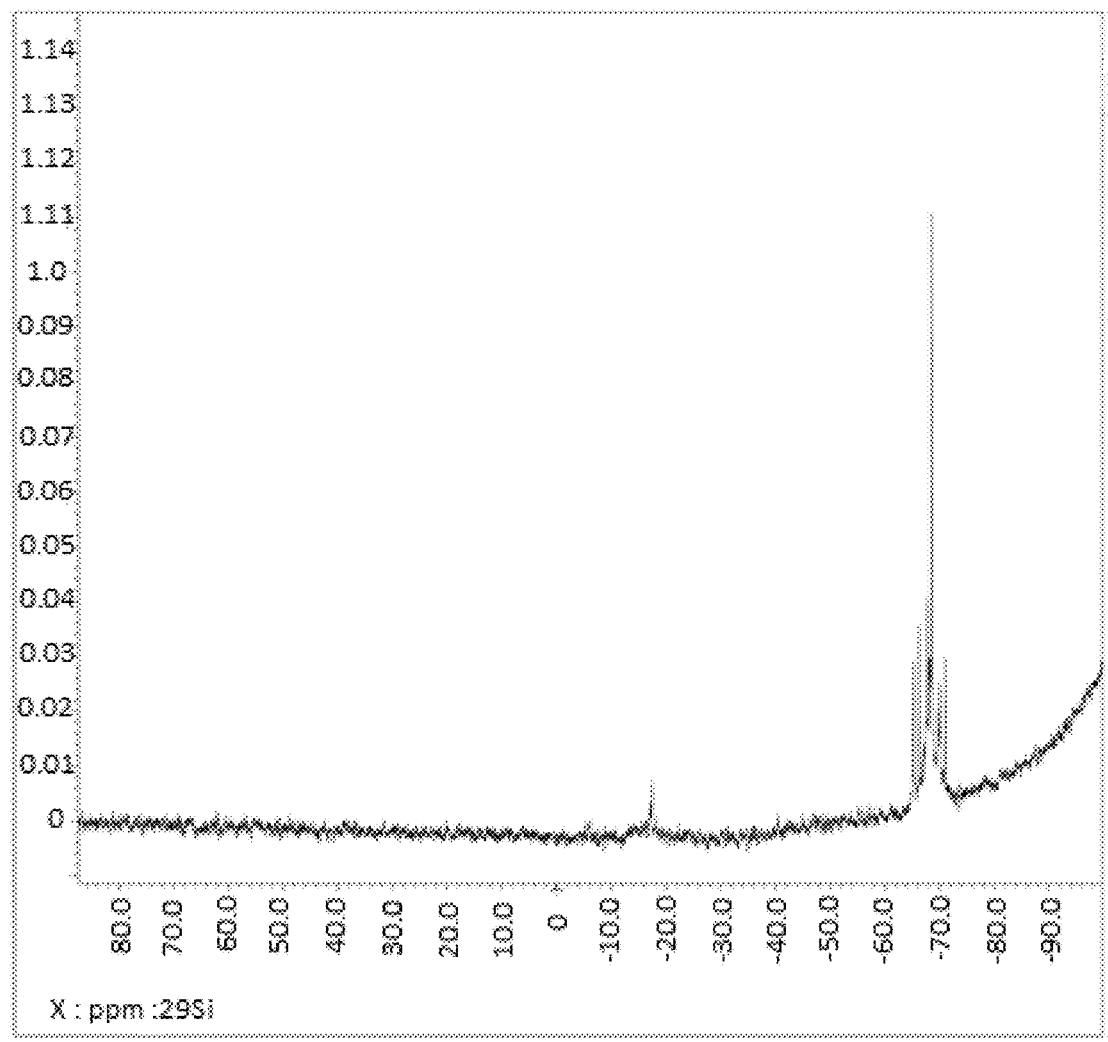
FIG. 13 is an analysis plot of $^{29}$Si NMR analysis for SB3 F-POSS methacrylate monomer according to Example 7.

$^1$H NMR showed a vinyl/methylene ratio of 1:20 possibly indicating formation of T10 or derivatives thereof. $^{19}$F NMR showed two sets of fluorine signals indicating the presence of both 4/2 and 6/2 components. $^{29}$Si NMR showed a small resonance at −17 ppm, but larger resonances between −60 and −71 ppm suggesting that there was more than one specific monomer component. (See FIGS. 11, 12 and 13). In FIG. 13, see resonances at −65.24, −66.16, −67.8, −68.51, −71.01 and −95.62.

Example 8

SB3 F-POSS-MA/Methylmethacrylate Polymer Synthesis

Four separate comparison reactions were run under the same conditions with varying amounts of SB3 F-POSS-MA.

A reaction vessel was charged with 25 mL of 4:1 hexafluorobenzene/THF and degassed for 20 minutes. To the vessel was added SB3 F-POSS-MA (either 0, 5, 10 or 15 weight percent), methylmethacrylate monomer (5 g total batch size) and 20 mg of 2,2'-azobis(2-methylpropionitrile) initiator. The reaction was run under nitrogen for 12 hours at 55° C., then 5 hours at 80° C. The reaction solution was poured into 150 mL of hexane and stirred with a spatula to break up the clumps. The solid material was filtered, washed thoroughly with hexane, and dried under high vacuum at 45° C. Polymer yields are shown in Table 3.

Polymer Yields:

TABLE 3

| Reaction | Yield |
|---|---|
| 0% SB3 F-POSS-MA monomer | 2.12 g |
| 5% SB3 F-POSS-MA monomer | 2.26 g |
| 10% SB3 F-POSS-MA monomer | 2.44 g |
| 15% SB3 F-POSS-MA monomer | 1.97 g |

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

As used in the specification and the appended claims, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. The word "exemplary" or "illustrative" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

It should further be noted that any patents, applications and publications referred to herein are incorporated by reference in their entirety.

We claim:

1. A process for preparing a derivatized F-POSS of the formula

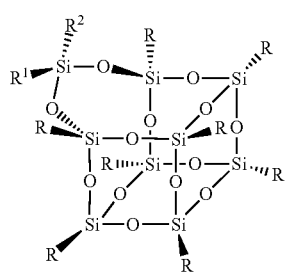

II comprising the step of contacting at least one F-POSS molecule of the formula

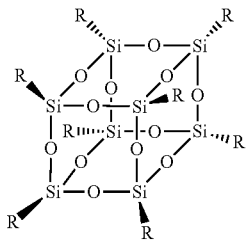

with a compound of the formula $R^1R^2Si(OR^3)_2$,
wherein
R is a long chain fluorinated alkyl;
$R^1$ and $R^2$ are each independently selected from the group consisting of $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^1$ and $R^2$ is independently optionally substituted by an $R^4$;
$R^3$ is a $C_1$-$C_8$ alkoxy;
each $R^4$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^5$, —$NR^5R^6$, —$OC(O)R^5$, —$C(O)OR^5$, —$C(O)R^5$, —$OC(O)OR^5$, —$C(O)NR^5R^6$, —$OC(O)NR^5R^6$, —$NR^5C(O)R^6$, —$NR^5C(O)OR^6$ and —$NR^5C(O)NR^5R^6$, and when $R^4$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^4$ is independently optionally substituted by an $R^7$;
each $R^5$ and $R^6$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, and 5-7 membered heteroaryl, wherein each hydrogen atom in $R^5$ and $R^6$ is independently optionally substituted by an $R^7$;
each $R^7$ is independently selected from the group consisting of halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^8$, —$NR^8R^9$, —$OC(O)R^8$, —$C(O)OR^8$, —$C(O)R^8$, —$OC(O)OR^8$, —$C(O)NR^8R^9$, —$OC(O)NR^8R^9$, —$NR^8C(O)R^9$, —$NR^8C(O)OR^9$ and —$NR^8C(O)NR^8R^9$, and when $R^7$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic or 5-7 membered heteroaryl, each hydrogen atom in $R^7$ is independently optionally substituted by an $R^{10}$;
each $R^8$ and $R^9$ is independently selected from the group consisting of hydrogen, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic and 5-7 membered heteroaryl, wherein each hydrogen atom in $R^8$ and $R^9$ is independently optionally substituted by one or more $R^{10}$;
each $R^{10}$ is independently selected from the group consisting of hydrogen, halo, $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, 5-7 membered heteroaryl, —NCO, —$OR^{11}$, —$NR^{11}R^{12}$, —$OC(O)R^{11}$, —$C(O)OR^{11}$, —$C(O)R^{11}$, —$OC(O)OR^{11}$, —$C(O)NR^{11}R^{12}$, —$OC(O)NR^{11}R^{12}$, —$NR^{11}C(O)R^{12}$, —$NR^{11}C(O)OR^{12}$ and —$NR^{11}C(O)NR^{11}R^{12}$, and when $R^{10}$ is $C_1$-$C_8$ alkyl, $C_2$-$C_8$ alkenyl, $C_2$-$C_8$ alkynyl, $C_6$-$C_{10}$ aryl, $C_3$-$C_8$ cycloalkyl, 5-7 membered heterocyclic, $C_3$-$C_8$ cycloalkyl or 5-7 membered heteroaryl, each hydrogen in $R^{10}$ is independently optionally substituted by a moiety selected from the group consisting of halo, —NCO, —$OR^{11}$, —$NR^{11}R^{12}$, —$OC(O)R^{11}$, —$C(O)OR^{11}$, —$C(O)R^{11}$, —$OC(O)OR^{11}$, —$C(O)NR^{11}R^{12}$, —$OC(O)NR^{11}R^{12}$, —$NR^{11}C(O)R^{12}$, —$NR^{11}C(O)OR^{12}$ and —$NR^{11}C(O)NR^{11}R^{12}$; and each $R^{11}$ and $R^{12}$ is independently selected from the group consisting of H, $C_1$-$C_8$ alkyl, $C_2$-$C_8$ alkenyl and $C_2$-$C_8$ alkynyl, and when $R^{11}$ or $R^{12}$ are $C_1$-$C_8$ alkyl, $C_2$-$C_8$ alkenyl or $C_2$-$C_8$ alkynyl, each hydrogen atom in $R^{11}$ and $R^{12}$ is independently optionally substituted by a fluorine atom,
in the presence of an aqueous base catalyst.

2. The process of claim 1, wherein $R^2$ is $C_1$-$C_8$ alkyl.

3. The process of claim 2, wherein $R^2$ is methyl.

4. The process of claim 2, wherein $R^1$ is $C_1$-$C_8$ alkyl, wherein each hydrogen atom in $R^1$ is independently optionally substituted by an $R^4$.

5. The process of claim 4, wherein $R^4$ is —NCO, —$OR^5$, —$OC(O)R^5$, —$C(O)OR^5$, —$C(O)R^5$ or —$OC(O)OR^5$.

6. The process of claim 5, wherein $R^5$ is $C_1$-$C_8$ alkyl, wherein each hydrogen atom in $R^5$ is independently optionally substituted by an $R^7$.

7. The process of claim 5, wherein $R^5$ is $C_2$-$C_8$ alkenyl, wherein each hydrogen atom in $R^5$ is independently optionally substituted by an $R^7$.

8. The process of claim 7, wherein R7 is C1-C8 alkyl, —NCO, —OR8, —NR8R9, —OC(O)R8, —C(O)OR8, —C(O)R8 or —OC(O)OR8.

9. The process of claim 8, wherein $R^8$ is $C_1$-$C_8$ alkyl, $C_2$-$C_8$ alkenyl, $C_2$-$C_8$ alkynyl, $C_6$-$C_{10}$ aryl or 5-7 membered heteroaryl, wherein each hydrogen atom in $R^8$ is independently optionally substituted by one or more $R^{10}$.

10. The process of claim 9, wherein $R^{10}$ is hydrogen or $C_1$-$C_8$ alkyl, and when $R^{10}$ is $C_1$-$C_8$ alkyl, $R^{10}$ is optionally substituted by a —$OC(O)R^{11}$.

11. The process of claim 10, wherein $R^{11}$ is H or $C_1$-$C_8$ alkyl, and when $R^{11}$ is $C_1$-$C_8$ alkyl, each hydrogen atom in $R^{11}$ is independently optionally substituted by a fluorine atom.

12. The process of claim 1, wherein $R^1$ is n-propyl, optionally substituted by an $R^4$.

13. The process of claim 10, wherein $R^4$ is —$OC(O)R^5$ or —$OC(O)OR^5$.

14. The process of claim 13, wherein $R^5$ is —CH=$CH_2$, optionally substituted by an $R^7$.

15. The process of claim 14, wherein $R^7$ is methyl.

16. The process of claim 1, wherein the aqueous base catalyst is an aqueous ammonium salt.

17. The process of claim 16, wherein the aqueous base catalyst is a tetraethylammonium salt.

18. The process of claim 17, wherein the aqueous base catalyst is tetraethylammonium hydroxide.

19. The process of claim 1, wherein the long chain fluorinated alkyl is 8/2, 6/2 or 4/2.

20. The process of claim 1, wherein the at least one F-POSS molecule is selected from the group consisting of 8/2 F-POSS, 6/2 F-POSS and 4/2 F-POSS.

* * * * *